US007456266B2

United States Patent
Bodepudi et al.

(10) Patent No.: US 7,456,266 B2
(45) Date of Patent: Nov. 25, 2008

(54) DETECTABLE LABELED NUCLEOSIDE ANALOGS AND METHODS OF USE THEREOF

(75) Inventors: Veeraiah Bodepudi, San Ramon, CA (US); Amar Gupta, Danville, CA (US); Stephen Gordon Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1 day.

(21) Appl. No.: 11/742,070

(22) Filed: Apr. 30, 2007

(65) Prior Publication Data

US 2007/0208169 A1    Sep. 6, 2007

Related U.S. Application Data

(62) Division of application No. 10/719,257, filed on Nov. 21, 2003, now Pat. No. 7,220,847.

(60) Provisional application No. 60/428,484, filed on Nov. 22, 2002.

(51) Int. Cl.
  *C07G 3/00*     (2006.01)
  *C07H 21/00*    (2006.01)
  *C07H 21/02*    (2006.01)
  *C12Q 1/68*     (2006.01)

(52) U.S. Cl. ............... 536/4.1; 536/23.1; 536/24.3; 536/25.3; 536/26.6; 435/6

(58) Field of Classification Search ............ 536/4.1, 536/23.1, 24.3, 25.3, 26.6; 435/6
  See application file for complete search history.

*Primary Examiner*—Jezia Riley
(74) *Attorney, Agent, or Firm*—Olga Kay; Charles M. Doyle

(57) ABSTRACT

The invention relates to detectable labels useful for detection of nucleotide sequences. Specifically, the invention relates to labeled-imidazole-PEG compounds, such as nucleosides, nucleotides, and nucleic acids incorporating such compounds, and methods utilizing such compounds. The invention further relates to kits comprising labeled imidazole-PEG compounds.

17 Claims, No Drawings

DETECTABLE LABELED NUCLEOSIDE ANALOGS AND METHODS OF USE THEREOF

1. CROSS-REFERENCE TO RELATED APPLICATION

This application claims the benefit under 37 C.F.R. §120 of U.S. application Ser. No. 10/719,257, filed Nov. 21, 2003 (Allowed), which application is incorporated by reference herein in its entirety.

2. FIELD OF THE INVENTION

The invention relates to detectable labels useful, for example, for the detection of nucleotide sequences. Specifically, the invention relates to labeled imidazole-PEG compounds, such as nucleosides, nucleotides, and nucleic acids incorporating such compounds, and methods utilizing such compounds. The invention further relates to kits comprising labeled imidazole-PEG compounds.

3. BACKGROUND OF THE INVENTION

Many procedures employed in biomedical research and recombinant DNA technology rely on the use of labeled nucleotide or polynucleotide derivatives. In order for a modified nucleotide to be generally suitable as a labeled form of a naturally occurring nucleotide, several criteria must typically be satisfied. First, the modified compound must contain a substituent or probe that is unique (i.e., not normally found associated with nucleotides or polynucleotides). Second, the probe must react specifically with chemical or biological reagents to provide a sensitive detection system. Third, the analog must be a relatively efficient substrate for commonly studied nucleic acid enzymes, since numerous practical applications require that the analog be enzymatically metabolized (e.g., the analog must function as a substrate for nucleic acid polymerases). For this purpose, probe moieties should not be placed on ring positions that sterically or otherwise interfere with the normal Watson Crick hydrogen bonding potential of the bases. In such cases, the substituents can yield compounds that are inactive as polymerase substrates. Fourth, the detection system should be capable of interacting with probe substituents incorporated into both single stranded and double stranded polynucleotides in order to be compatible with nucleic acid hybridization methodologies. Fifth, the physical and biochemical properties of polynucleotides containing small numbers of probe substituents should not be significantly altered so that current procedures using hybridization probes need not be extensively modified. This criterion must be satisfied whether the probe is introduced by enzymatic or direct chemical means. Finally, the linkage that attaches the probe moiety should withstand all experimental conditions to which normal nucleotides and polynucleotides are routinely subjected (e.g., extended hybridization times at elevated temperatures, phenol and organic solvent extraction, or electrophoresis).

The specificity and tenacity of the biotin avidin complex has been used in recent years to develop methods for visually localizing specific proteins, lipids, or carbohydrates on or within cells (E. A. Bayer and M. Wilchek, *Methods of Biochemical Analysis*, 26, 1, 1980). Chromosomal location of RNA has been determined by electron microscopy using a biotinized protein (e.g., cytochrome C) chemically crosslinked to RNA as a hybridization probe. The site of hybridization was visualized through the binding of avidin ferritin or avidin methacrylate spheres mediated by the avidin biotin interaction. (Manning et al., 1975, *Chromosoma*, 53: 107; Manning, 1977, *Biochemistry*, 61: 1364; Broker, 1978, *Nucleic Acid Res.*, 5: 363; and Sodja 1978, et al., *Nucleic Acid Res.*, 5: 383). This approach to the detection of polynucleotide sequences, although successful in the specialized cases examined, which were highly reiterated sequences, is not of general utility for analysis of polynucleotides present in single or low copy number.

Accordingly, there remains a continuing need for detectable labeled compounds that are safe, cost effective, stable, efficient, and provide for sensitive detection.

4. SUMMARY OF THE INVENTION

The invention provides a series of novel nucleotide derivatives that contain a label covalently attached to an imidazole compound. In one aspect, the invention relates to a class of compounds that are useful as labels for detection of nucleotide sequences. In another aspect, the invention relates to oligonucleotides comprising a detectable label. The invention further relates to methods of use and methods of making the detectable labels of the invention.

The invention encompasses compounds of formula I:

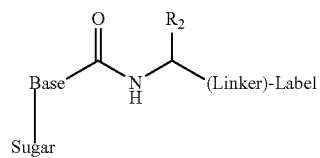

I alone or in combination with a counterion thereof or a stable salt, solvate, clathrate or mixture thereof, wherein:

sugar is a ribose, deoxyribose or a ribose sugar analog;

base is

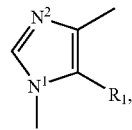

wherein the sugar is covalently bonded to $N^1$ of the base;

wherein $R_1$ is —H, —NHC(O)$NH_2$, —$NH_2$, —OH, —O(alkyl), alkyl, $CO_2H$;

wherein $R_2$ is —H, —$NH_2$, —OH, —O(alkyl), alkyl, $CO_2H$, —$CO_2$alkyl;

linker is any linker known to those of skill in the art; and label is any label known to those of skill in the art. In one embodiment the linker is (—O-alkyl)$_n$, (NH)$_n$, (C(O)NH)$_n$, (NHC(O)NH)$_n$, (NH-alkyl-O-alkyl-NH)$_n$, or (alkyl)$_n$; wherein n is an integer from 1 to 30. In one embodiment, label is a colorimetric compound, a chemiluminescent compound, a bioluminescent compound, a quencher, a fluorescent compound or a non- or weakly fluorescent compound (each compound being a "detectable label").

The invention also encompasses oligonucleotides comprising a detectable label of formula II:

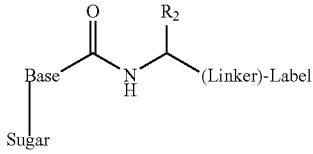

alone or in combination with a counterion thereof or a stable salt, solvate, clathrate or mixture thereof, wherein:
sugar is a ribose, deoxyribose or a ribose sugar analog;
base is

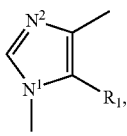

wherein the sugar is covalently bonded to $N^1$ of the base;
wherein $R_1$ is —H, —NHC(O)NH$_2$, —NH$_2$, —OH, —O(alkyl), alkyl, CO$_2$H;
wherein $R_2$ is —H, —NH$_2$, —OH, —O(alkyl), alkyl, CO$_2$H, —CO$_2$alkyl;
linker is any linker known to those of skill in the art; and
label is any label known to those of skill in the art. In one embodiment linker is (alkylO)$_n$, (NH)$_n$, (C(O)NH)$_n$, (NHC(O)NH)$_n$, (NH-alkyl-O-alkyl-NH)$_n$, or (alkyl)$_n$; wherein n is an integer from 1 to 30. In one embodiment, label is a colorimetric compound, a chemiluminescent compound, a bioluminescent compound, a quencher, a fluorescent compound or a non- or weakly fluorescent compound.

Another embodiment encompasses a method for detecting the presence or absence of a target nucleic acid in a test sample, comprising:
contacting the test sample with a composition comprising an oligo- or polynucleotide probe wherein the oligo- or polynucleotide probe comprises a detectable label of formula:

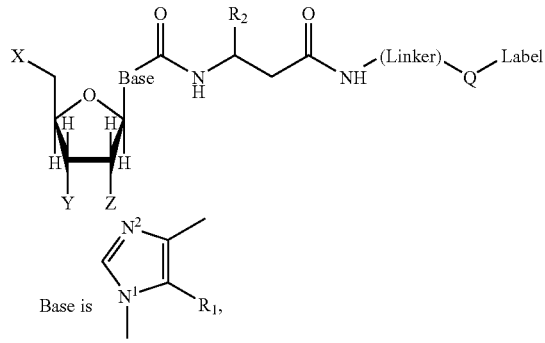

wherein the sugar is covalently bonded to $N^1$ of the base;
wherein $R_1$ is —H, —NHC(O)NH$_2$, —NH$_2$, —OH, —O(alkyl), alkyl, CO$_2$H;
wherein $R_2$ is —H, —NH$_2$, —OH, —O(alkyl), alkyl, CO$_2$H, —CO$_2$alkyl;
each of X, Y, and Z is independently —H, —OH, —O(alkyl), —SH, —SR$_4$, —NHR$_4$, NR$_4$R$_5$,

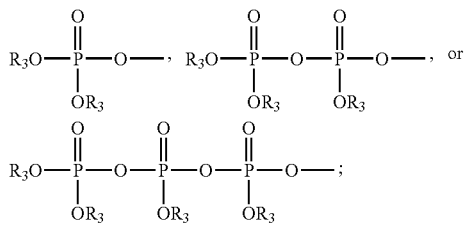

wherein $R_3$ is —H or metal;
$R_4$ is —H or alkyl;
$R_5$ is —H or alkyl;
Q is O, S, or NH;
linker is any linker known to those of skill in the art;
label is any label known to those of skill in the art;
wherein the oligonucleotide probe is capable of selectively or specifically hybridizing with the target nucleic acid under conditions of moderate stringency;
optionally exposing the sample to light of said excitable wavelength; and
detecting whether said contacting produces a change in color or fluorescence emission of the composition;
such that a change in color or fluorescence emission of the composition indicates that the target nucleic acid is present in the test sample. In one embodiment, label is a colorimetric compound, a chemiluminescent compound, a bioluminescent compound, a quencher,
a fluorescent compound or a non- or weakly fluorescent compound.

Another embodiment encompasses method for detecting ribonuclease activity in a test sample, comprising:
contacting the test sample with a substrate, thereby creating a test reaction mixture, wherein said substrate comprises a nucleic acid molecule comprising:
i. a cleavage domain comprising a single stranded region, said single stranded region comprising at least one internucleotide linkage immediately 3' to an adenosine residue, at least one internucleotide linkage immediately 3' to a cytosine residue, at least one internucleotide linkage immediately 3' to a guanosine residue, and at least one internucleotide linkage immediately 3' to a uridine residue, and wherein said cleavage domain does not comprise a deoxyribonuclease cleavable internucleotide linkage; and
ii. a detectable label of the invention on one side of at least one of the internucleotide linkages;
incubating said test reaction mixture for a time sufficient for cleavage of the substrate by a ribonuclease in the sample; and
determining whether a detectable signal is emitted from the test reaction mixture,
wherein emission of a detectable signal from the reaction mixture indicates that the sample contains ribonuclease activity.

Another embodiment encompasses a method for detecting ribonuclease activity in a test sample, comprising;
contacting the test sample with a substrate, thereby creating a test reaction mixture, wherein said substrate comprises a nucleic acid molecule comprising:
i. a cleavage domain comprising a single stranded region, said single stranded region comprising at least one internucleotide linkage immediately 3' to an adenosine residue, at least one internucleotide linkage immediately 3' to a cytosine residue, at least one internucleotide linkage immediately 3' to a guanosine residue, and at least one internucleotide linkage immediately 3' to a uridine residue, and wherein said cleavage domain does not comprise a deoxyribonuclease cleavable internucleotide linkage; and ii. a detectable label on one side of at least one of the internucleotide linkages;

incubating said test reaction mixture for a time sufficient for cleavage of the substrate by a ribonuclease activity in the test sample;

determining whether a detectable signal is emitted from the test reaction mixture;

contacting a control sample with the substrate, said control sample comprising a predetermined amount of ribonuclease, thereby creating a control reaction mixture;

incubating said control reaction mixture for a time sufficient for cleavage of the substrate by a ribonuclease in the control sample;

determining whether a detectable signal is emitted from the control reaction mixture;

wherein detection of a greater signal in the test reaction mixture than in the control reaction mixture indicates that the test sample contains greater ribonuclease activity than in the control sample, and wherein detection of a lesser signal in the test reaction mixture than in the control reaction mixture indicates that the test sample contains less ribonuclease activity than in the control sample, and wherein detection of a signal in the test reaction mixture equal to that in the control reaction mixture indicates that the test sample contains the same amount of ribonuclease activity as is present in the control sample.

Another embodiment encompasses methods of making a compound of formula I:

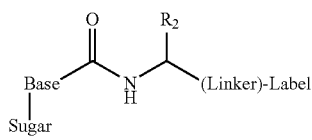

I alone or in combination with a counterion thereof or a stable salt, solvate, clathrate or mixture thereof, wherein:
sugar is a ribose, deoxyribose or a ribose sugar analog;
base is

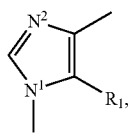

wherein the sugar is covalently bonded to $N^1$ of the base,
wherein $R_1$ is —H, —NHC(O)NH$_2$, —NH$_2$, —OH, —O(alkyl), alkyl, CO$_2$H;
wherein $R_2$ is —H, —NH$_2$, —OH, —O(alkyl), alkyl, CO$_2$H, —CO$_2$alkyl;
linker is any linker known to those of skill in the art; and
label is any label known to those of skill in the art. In one embodiment linker is (alkylO)$_n$, (NH)$_n$, (C(O)NH)$_n$, (NHC(O)NH)$_n$, (NH-alkyl-O-alkyl-NH)$_n$, or (alkyl)$_n$; wherein n is an integer from 1 to 30. In one embodiment, label is a colorimetric compound, a chemiluminescent compound, a bioluminescent compound, a quencher, a fluorescent compound or a non- or weakly fluorescent compound.

Another embodiment encompasses a method of detecting endonuclease activity in a test sample comprising:

contacting the test sample with a substrate, thereby creating a test reaction mixture, wherein said substrate comprises a nucleic acid molecule comprising a detectable label and a quencher;

incubating the test reaction mixture for a time sufficient for cleavage of the substrate by endonuclease activity in the test sample to separate the detectable label from the quencher;

determining whether a detectable signal is emitted from the test reaction mixture;

contacting a control sample with the substrate, the control sample comprising a predetermined amount of endonuclease, thereby creating a control reaction mixture;

incubating the control reaction mixture for a time sufficient for cleavage of the substrate by an endonuclease in the control sample;

determining whether a detectable signal is emitted from the control reaction mixture;

wherein detection of a greater signal in the test reaction mixture than in the control reaction mixture indicates that the test sample contains greater endonuclease activity than in the control sample, and wherein detection of a lesser signal in the test reaction mixture than in the control reaction mixture indicates that the test sample contains less endonuclease activity than in the control sample, and wherein detection of a signal in the test reaction mixture equal to that in the control reaction mixture indicates that the test sample contains the same amount of endonuclease activity as is present in the control sample.

Another embodiment encompasses a method of making a labeled polynucleotide comprising:

contacting a double or single stranded nucleotide with a terminal deoxynucleotidyl transferase under conditions suitable to afford a 3' hydroxyl terminus;

contacting with a detectable label of the invention, under conditions suitable for the attachment of a compound to a 3' hydroxyl terminus of the double or single stranded nucleotide to afford a labeled nucleotide; and detecting the labeled nucleotide.

Another embodiment encompasses a method for detecting ribonuclease activity in a test sample, comprising:

contacting the test sample with a substrate, thereby creating a test reaction mixture, wherein the substrate comprises a nucleic acid molecule comprising:

i. a cleavage domain comprising a single stranded region, the single stranded region comprising at least one internucleotide linkage immediately 3' to an adenosine residue, at least one internucleotide linkage immediately 3' to a cytosine residue, at least one internucleotide linkage immediately 3' to a guanosine residue, and at least one internucleotide linkage immediately 3' to a uridine residue, and wherein the cleavage domain does not comprise a deoxyribonuclease-cleavable internucleotide linkage; and ii. a detectable label on one side of the internucleotide linkages;

incubating the test reaction mixture for a time sufficient for cleavage of the substrate by a ribonuclease activity in the test sample;

determining whether a detectable signal is emitted from the test reaction mixture, contacting a control sample with the substrate, the control sample comprising a predetermined amount of ribonuclease, thereby creating a control reaction mixture;

incubating the control reaction mixture for a time sufficient for cleavage of the substrate by a ribonuclease in the control sample;

determining whether a detectable signal is emitted from the control reaction mixture;

wherein detection of a greater signal in the test reaction mixture than in the control reaction mixture indicates that the test sample contains greater ribonuclease activity than in the control sample, and wherein detection of a lesser signal in the test reaction mixture than in the control reaction mixture indicates that the test sample contains less ribonuclease activity than in the control sample, and wherein detection of a signal in the test reaction mixture equal to that in the control reaction mixture indicates that the test sample contains the same.

4.1 Definitions

As used herein and unless otherwise indicated, the term "alkyl group" means a saturated, monovalent, unbranched or branched hydrocarbon chain. Examples of alkyl groups include, but are not limited to, $C_1$-$C_6$ alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2 pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term —O-alkyl (or alkyl-O—) means an "alkoxy group," wherein alkyl is as defined above. An alkoxy group can be unsubstituted or substituted with one or more suitable substituents. The alkyl chain of an alkyloxy group can be, for example, from 1 to 6 carbon atoms in length.

As used herein and unless otherwise indicated, the term "metal" refers to a group I or group II metal, including but not limited to, $Li^+$, $Na^+$, $Ca^{2+}$, or $Mg^{2+}$.

As used herein and unless otherwise indicated, the term "substituted" refers to a radical in which one or more hydrogen atoms are each independently replaced with the same or different substituent(s). Typical substituents include, but are not limited to, alkyl, alkoxy, —X, —R, —O, =O, —OR, —O—OR, —SR, —S, =S, —NRR, =NR, —CX$_3$, —CN, —OCN, —SCN, —NCO, —NCS, —NHCHO, —NHCOC$_1$-C$_4$alkyl, —NHCOCH$_3$, —NHCOCH$_2$Cl, —NHCOCHCl$_2$, —NHCOCCl3, —NHCOCF$_3$, —NHCOCH$_2$C$_6$H$_4$-o-NO$_2$, NHCOCH$_2$OC$_6$H$_4$-o-NO$_2$, where each X is independently a halogen (preferably —F, —Cl or —Br) and each R is independently —H, alkyl, alkenyl, alkynyl, aryl, arylalkyl, arylheteroalkyl, heteroaryl, heteroarylalkyl or heteroaryl heteroalkyl, as defined herein.

As used herein and unless otherwise indicated, the term "linking group" and "linker" are used interchangeably and refer to a moiety of a detectable label capable of covalently bonding a base with a label, e.g., forming a "linkage" that connects the nucleoside, nucleotide or nucleic acid to the label. Examples of linkers include, but are not limited to, O, S, or NH. Optionally, the linking group or linker is a covalent bond (i.e., the label is covalently bonded to the base).

As used herein and unless otherwise indicated, the term "counterion" refers to an ion that is stable and synthetically accessible. Examples of counterions include, but are not limited to, chloride, bromide, iodide, sulfate, benzene sulfonate, p-toluenesulfonate, p-bromobenzenesulfonate, methanesulfonate, trifluoromethanesulfonate, phosphate, perchlorate, tetrafluoroborate, tetraphenylboride, nitrate and anions of aromatic or aliphatic carboxylic acids. Preferred counterions are chloride, iodide, perchlorate and the sulfonates listed above.

As used herein, a substance that is "biologically compatible" is not toxic as used, and does not have a substantially deleterious effect on biomolecules.

As used herein and unless otherwise indicated, the terms "biotin" or "biotin derivative" refer respectively to biotin or a compound wherein one of the atoms of biotin is replaced with another suitable atom; examples of suitable atoms include, but are not limited to, —O, —N, —P, or —S. Examples of biotin or a biotin derivative include, but are not limited to, biotin or iminobiotin, which have the following respective structures:

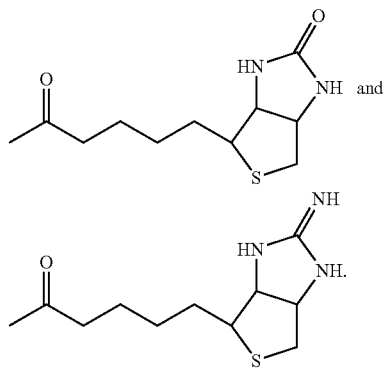

As used herein and unless otherwise indicated, the term "nucleobase" refers to adenine, cytidine, guanine, thymine or uracil.

As used herein and unless otherwise indicated, the term "nucleobase analog" refers to a substituted or unsubstituted nitrogen-containing parent heteroaromatic ring that is capable of forming Watson-Crick hydrogen bonds with a complementary nucleobase or nucleobase analog. Preferably, the nucleobase analog is a purine, deazapurine or pyrimidine. Exemplary nucleobase analogs include, but are not limited to, 7-deazaadenine, inosine, nebularine, nitropyrrole, nitroindole, 2-aminopurine, 2,6-diaminopurine, hypoxanthine, pseudouridine, 5-propynylcytidine, isocytidine, isoguanine, 7-deazaguanine, 2-thiopyrimidine, 6-thioguanine, 4-thiothymine, 4-thiouracil, $O^6$-methyl guanine, $N^6$-methyl adenine, $O^4$-methyl thymine, 5,6-dihydrothymine, 5,6-dihydrouracil, 4-methylindole, ethenoadenine, etc. Additional exemplary nucleobase analogs can be found in Fasman, 1989, *Practical Handbook of Biochemistry and Molecular Biology*, pp. 385-394, CRC Press, Boca Raton, Fla., and the references cited therein, incorporated herein by reference.

As used herein and unless otherwise indicated, the term "nucleoside" refers to a compound consisting of a nucleobase covalently linked to the C1' carbon of a substituted or unsubstituted ribose sugar. Typical substituted ribose sugars include, but are not limited to, those in which one or more of its carbon atoms, preferably one and most preferably the 3' carbon atom, is substituted with one or more of the same or different —R, —OR, —NRR or halogen groups, where each R is independently —H, ($C_1$-$C_6$) alkyl or ($C_5$-$C_{14}$) aryl. Particularly preferred ribose sugars are ribose, 2'-deoxyribose, 2',3'-dideoxyribose, 3'-haloribose, 3'-fluororibose, 3'-chlororibose, 3'-alkylribose, etc. When the nucleobase is A or G, the ribose sugar is attached to the $N^9$ position of the nucleobase. Where the nucleobase is C, T or U, the pentose sugar is attached to the $N^1$ position of the nucleobase (see, e.g., Kornberg and Baker, 1992, *DNA Replication,* 2nd Ed., Freeman, San Francisco).

As used herein and unless otherwise indicated, the term "nucleoside analog" refers to a nucleoside in which the nucleobase, the ribose sugar, or both, are replaced with their respective analogs. Exemplary nucleobase analogs are those previously defined. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, OR, —NRR or halogen groups, where each R is independently —H, ($C_1$-$C_6$) alkyl or ($C_5$-$C_{14}$) aryl.

As used herein and unless otherwise indicated, the term "nucleotide" refers to a nucleoside in which one or more, typically one, of the ribose carbons is substituted with a phosphate ester having the formula:

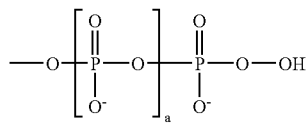

where a is an integer from 0 to 4. Preferably, a is 2 and the phosphate ester is attached to the 3' or 5' carbon of the ribose, e.g., ribose 3'-triphosphate, 2'-deoxyribose 3-triphosphate, ribose 5'-triphosphate, 2'-deoxyribose 5'-triphosphate, 3'-haloribose 5'-triphosphate, 3'-alkylribose 5'-triphosphate, 2',3'-dideoxyribose 5'-triphosphate, etc.

As used herein and unless otherwise indicated, the term "nucleotide derivative" refers to a nucleotide in which the nucleobase, the ribose sugar and/or one or more of the phosphate esters is replaced with its respective analog. Exemplary nucleobase and ribose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, peptide nucleic acid (PNA) monomers, etc., including any associated counterions, if present.

As used herein and unless otherwise indicated, the term "protecting group" means a group that is reversibly attached to a hydroxyl or amine moiety that renders the hydroxyl or amine moiety unreactive during a subsequent reaction(s) and that can be selectively cleaved to regenerate the hydroxyl or amine moiety once its protecting purpose has been served. Examples of protecting groups are found in Greene, T. W., *Protective Groups in Organic Synthesis,* 3rd edition (1999), incorporated herein by reference. In one embodiment, the protecting group is stable in a basic reaction medium, but can be cleaved by acid. Examples of base-stable acid-labile protecting groups suitable for use with the invention include, but are not limited to, ethers, such as methyl, methoxy methyl, methylthiomethyl, methoxyethoxymethyl, bis(2 chloroethoxy)methyl, tetrahydropyranyl, tetrahydrothiopyranyl, tetrahydrofuranyl, tetrahydrothiofuranyl, 1-ethoxyethyl, 1-methyl 1-methoxyethyl, t-butyl, allyl, benzyl, o-nitrobenzyl, triphenylmethyl, α-naphthyldiphenylmethyl, p-methoxyphenyldiphenylmethyl, 9-(9-phenyl-10-oxo)anthranyl, trimethylsilyl, isopropyldimethylsilyl, t-butyldimethylsilyl, t-butyldiphenylsilyl, tribenzylsilyl, and triisopropylsilyl; and esters, such as pivaloate, adamantoate, and 2,4,6-trimethylbenzoate.

As used herein and unless otherwise indicated, the term "salt(s)," includes, but is not limited to, salts of acidic or basic groups that may be present in the compounds of the invention. Compounds that are basic in nature are capable of forming a wide variety of salts with various inorganic and organic acids. The acids that may be used to prepare acceptable acid addition salts of such basic compounds are those that form non-toxic acid addition salts, i.e., salts containing pharmacologically acceptable anions, including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartarate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p toluenesulfonate and pamoate (i.e., 1,1'-methylene-bis-(2-hydroxy-3-naphthoate)) salts. Compounds of the invention that include an amino moiety also can form acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein and unless otherwise indicated, the term "solvate" means a compound of the invention or a salt thereof, that further includes a stoichiometric or non stoichiometric amount of a solvent bound by non-covalent intermolecular forces. Preferred solvents are volatile and non-toxic. The term solvate includes hydrates. Hydrate means a compound of the invention or a salt thereof, that further includes a stoichiometric or non-stoichiometric amount of water bound by non-covalent intermolecular forces.

As used herein and unless otherwise indicated, the term "clathrate" means a compound of the invention or a salt thereof in the form of a crystal lattice that contains spaces (e.g., channels) that have a guest molecule (e.g., a solvent or water) trapped within.

As used herein and unless otherwise indicated, the term "nucleoside or nucleotide" refers to nucleosides and/or nucleotides and/or mixtures thereof.

"Nucleoside analog" refers to a nucleoside in which the nucleobase, the ribose sugar, or both, are replaced with their respective analogs. Exemplary nucleobase analogs are those previously defined. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently H, $C_1$-$C_6$ alkyl or $C_5$-$C_{14}$ aryl.

As used herein and unless otherwise indicated, the term "nucleotide" refers to a nucleoside in which one or more, typically one, of the ribose carbons is substituted with a phosphate ester having the formula:

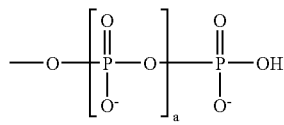

where a is an integer from 0 to 4. Preferably, a is 2 and the phosphate ester is attached to the 3'- or 5'-carbon of the ribose, e.g., ribose 3'-triphosphate, 2'-deoxyribose 3'-triphosphate, ribose 5'-triphosphate, 2'-deoxyribose 5'-triphosphate, 3'-haloribose 5'-triphosphate, 3'-alkylribose 5'-triphosphate, 2',3'-dideoxyribose 5'-triphosphate, etc.

As used herein and unless otherwise indicated, the term "nucleotide analog" refers to a nucleotide in which the nucleobase, the ribose sugar and/or one or more of the phosphate esters is replaced with its respective analog. Exemplary nucleobase and ribose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, peptide nucleic acid (PNA) monomers, etc., including any associated counterions, if present.

As used herein and unless otherwise indicated, the term "nucleic acid" refers to a linear polymeric chain of nucleoside monomer units that are covalently connected to one another by phosphate ester internucleotide linkages. Unless stated otherwise, "nucleic acid" as used herein includes polymers of any length, including oligonucleotides, nucleic acids and nucleic acids as those terms are commonly used in the art. Thus, nucleic acids according to the invention can range in size from a few monomer units (e.g., 4 to 40), to several hundreds of monomer units, to several thousands of monomer units, or even more monomer units. Such nucleic acids can also be described herein in terms of their functions, such as primer or probe. Whenever a nucleic acid is represented by a sequence of letters, e.g., "ATGCCTG," it will be understood that the sequence is presented in the 5'→3' direction. Unless otherwise indicated, nucleic acids whose sequences are described herein are 2'-deoxyribonucleic acids.

As used herein and unless otherwise indicated, the term "nucleic acid analog" refers to a nucleic acid in which at least one nucleoside monomer unit is a "nucleoside analog" and/or at least one phosphate ester internucleotide linkage is a phosphate ester analog, as defined above under "nucleotide analog." Preferred classes of nucleic acid analogs are those in which the sugar and internucleotide linkages are replaced with an uncharged, neutral amide, such as a morpholino carbamate and peptide nucleic acids ("PNA"). Preferred PNAs are those having a N-(2-aminoethyl) glycine amide backbone (see, e.g., Nielsen et al., 1991, *Science* 254:1497-1500).

As used herein and unless otherwise indicated, the term "label" refers to a detectable molecule or atom attached, covalently or non-covalently, to a nucleoside or nucleotide, nucleoside or nucleotide analog, nucleic acid, nucleic acid analog or terminator. In one embodiment, a nucleoside or nucleotide, nucleoside or nucleotide analog, nucleic acid, nucleic acid analog or terminator has a detectable label covalently attached to the nucleobase. The term "label" can also refer to a molecule that modulates detection of another detectable label, such as a quencher. As used herein, the term "detectable label" is intended to include not only a molecule or label which is "directly" detected (e.g., a chromogen or a fluorophore) but also a moiety (e.g., biotin) which is "indirectly" detected by its binding to a second, third, or greater binding partner (e.g., avidin or streptavidin), one of which carries a "direct" label. In one embodiment, the oligonucleotide is biotin-modified, and is detectable using a detection system based on avidin or streptavidin which binds with high affinity to biotin. The avidin or streptavidin can be conjugated to an enzyme, the presence of which is detected by allowing the enzyme to react with a chromogenic substrate and measuring the color developed (i.e., "colorimetric compound"). Non-limiting examples of useful enzymes in the methods of the present invention are horseradish peroxidase (HRP), alkaline phosphatase, glucose-6-phosphate dehydrogenase, malate dehydrogenase, staphylococcal nuclease, delta-V-steroid isomerase, yeast alcohol dehydrogenate, α-glycerophosphate dehydrogenase, triose phosphate isomerase, asparaginase, glucose oxidase, β-galactosidase, ribonuclease, urease, catalase, glucoamylase and acetylcholinesterase.

Other examples of labels include a fluorescent compound, which when exposed to light of the proper wavelength, becomes detectable due to fluorescence and is detected and/or measured by microscopy or fluorometry. Commonly used fluorescent labeling compounds include fluorescein isothiocyanate, rhodamine, phycoerythrin, phycocyanin, allophycocyanin, γ-phthaldehyde and fluorescamine. The detectable label can be a fluorescence-emitting metal such as $^{152}$Eu, or others of the lanthanide series which can be attached to the oligonucleotide using metal chelating groups, such as diethylenetriaminepentaacetic acid or ethylenediaminetetraacetic acid.

The label can be a chemiluminescent compound, the presence of which is detected by measuring luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound can be used to label the oligonucleotide and is detected by measuring luminescence. In this case, a catalytic protein increases the efficiency of the chemiluminescence reaction. Examples of useful bioluminescent labeling compounds include luciferin, luciferase and aequorin.

As used herein and unless otherwise indicated, the term "reporter dye" refers to a compound which, when exposed to light, emits energy in the form of fluorescence. "The chromophore of a reporter dye" is the network of atoms of the reporter dye that, when exposed to light, emits radiation at a level that is detectable by conventional spectroscopic means.

As used herein and unless otherwise indicated, the term "non-fluorescent" refers to a compound that, when exposed to radiation, does not emit radiation at a level that is detectable by conventional spectroscopic means.

As used herein and unless otherwise indicated, the term "weakly fluorescent" refers to a compound that, when exposed to radiation, emits radiation at a low level that is detectable by conventional spectroscopic means.

As used herein and unless otherwise indicated, the term "light" refers to electromagnetic energy having a wavelength which causes a reporter dye to fluoresce, wherein that wavelength may be in the range of 190-800 nm.

As used herein and unless otherwise indicated, the term "specific" refers to a nucleic acid used in a reaction, such as a probe used in a hybridization reaction, a primer used in a PCR, or a nucleic acid present in a composition, that hybridizes only with the intended target but not to other nucleic acid molecules in the test sample in the normal testing environment.

As used herein and unless otherwise indicated, the term "selective" refers to a nucleic acid used in a reaction, such as a probe used in a hybridization reaction, a primer used in a PCR, or a nucleic acid present in a pharmaceutical preparation, that hybridizes with the intended target more frequently, more rapidly, or with greater duration than it does with other nucleic acids in the test sample in the normal testing environment.

As used herein, the term "hybridizes under stringent conditions" describes conditions for hybridization and washing under which nucleotide sequences at least 60% (65%, 70%, or 75% or greater) identical to each other typically remain hybridized to each other. Stringent conditions depend on the nature of the nucleic acid (e.g. length, GC content, etc.) and the method itself (hybridization, amplification, etc.). Such methods are well known in the art and can be found in *Current Protocols in Molecular Biology*, John Wiley & Sons, N.Y. (1989), 6.3.1-6.3.6. In one embodiment, stringent hybridization conditions are hybridization at 6× sodium chloride/sodium citrate (SSC) at about 45° C., followed by one or more washes in 0.1×SSC, 0.2% SDS at about 68° C. In another embodiment, stringent hybridization conditions are hybridization in 6×SSC at about 45° C., followed by one or more washes in 0.2×SSC, 0.1% SDS at 50 65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides. For example, stringent hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris HCl, a $Mg^{2+}$ concentration of 1.5 mM, a pH of 7-7.5 and an annealing temperature of 55-60° C. Moderate stringency hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris HCl, a $Mg^{2+}$ concentration of 1.5 mM, a pH of 7-7.5 and an annealing temperature of 48-54° C. Low stringency hybridization of an oligonucleotide of approximately 15-40 bases to a complementary sequence in the polymerase chain reaction (PCR) can be performed under the following conditions: a salt concentration of 50 mM KCl, a buffer concentration of 10 mM Tris HCl, a $Mg^{2+}$ concentration of 1.5 mM, a pH of 7-7.5 and an annealing temperature of 37-47° C.

As used herein and unless otherwise indicated, the term "stereomerically pure" refers to a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "substantially free" refers to a composition that comprises one compound and is free of detectable or significant quantities of other compounds. A typical substantially free composition comprises greater than about 80% by weight of the desired compound and less than about 20% by weight of one or more other compounds, more preferably greater than about 90% by weight of the desired compound and less than about 10% by weight of one or more other compounds, even more preferably greater than about 95% by weight of the desired compound and less than about 5% by weight of one or more other compounds, and most preferably greater than about 97% by weight of the desired compound and less than about 3% by weight of one or more other compounds.

4.2 Abbreviations

The abbreviations used throughout the specification to refer to certain nucleobases and nucleosides or nucleotides are those commonly employed in the art and are as follows:

| Expression | Abbreviation |
| --- | --- |
| adenine | A |
| cytosine | C |
| guanine | G |
| thymine | T |
| uracil | U |
| ribonucleoside 5' triphosphate | NTP |
| adenosine 5' triphosphate | ATP |
| cytidine 5' triphosphate | CTP |
| guanosine 5' triphosphate | GTP |
| thymidine 5' triphospate | TTP |
| uridine 5' triphosphate | UTP |
| 2' deoxyribonucleoside 5' triphosphate | dNTP |
| 2' deoxyriboadenosine 5' triphosphate | dATP |
| 2' deoxyribocytidine 5' triphosphate | dCTP |
| 2' deoxyriboguanosine 5' triphosphate | dGTP |
| 2' deoxyribothymidine 5' triphospate | dTTP |
| 2' deoxyribouridine 5' triphosphate | dUTP |
| 2',3' dideoxyribonucleoside 5' triphosphate | ddNTP |
| 2',3' dideoxyriboadenosine 5' triphosphate | ddATP |
| 2',3' dideoxyribocytidine 5' triphosphate | ddCTP |
| 2',3' dideoxyriboguanosine 5' triphosphate | ddGTP |
| 2',3' dideoxyribothymidine 5' triphosphate | ddTTP |
| 2',3' dideoxyribouridine 5' triphosphate | ddUTP |

The following additional abbreviations are used in the specification.

The abbreviations used throughout the specification are those commonly employed in the art and are as follows:

| Term | Abbreviation |
| --- | --- |
| 2-[4-(2-chloro-4nitrophenylazo)-N-ethylphenylamino]ethanol | Disperse Red '3 |
| 6-carboxyfluorescein | 6Fam |
| N,N,N',N'-tetramethyl-6-carboxyrhodamine | TAMRA |
| 6-carboxytetramethylrhodamine | 6Tamra |
| Indodicarbocyanine 3 | Cy3 |
| Indodicarbocyanine 5 | Cy5 |
| Indodicarbocyanine 5.5 | Cy5.5 |
| 3-(ε-carboxy pentyl)-3'-ethyl-5,5'-dimethyloxacarbocyanine | CyA |
| 5-[(2-aminoethyl)amino]napthalene-1-sulfonic acid | EDANS |
| tetrachlorofluorescein | TET |
| 2',7'-dimethoxy-4',5'-dichloro-6-carboxy-fluorescein | JOE |
| 6-carboxy-X-rhodamine | ROX |
| 1H,5H,11H,15H-Xantheno[2,3,4 ij:5,6,7 i'j']diquinolizin-18- | TR or |

-continued

| Term | Abbreviation |
|---|---|
| ium, 9-[2(or 4)[[[6[2,5-dioxo-1-pyrrolidinyl)oxy]-6-oxohexyl]amino]sulfonyl]-4(or 2)-sulfophenyl]-2,3,6,7,12,13,16,17-octahydro-, inner salt | Texas Red |
| N,N'-dimethyl-N,N'-diphenyl-4-((5-t-butoxycarbonylaminopentyl)aminocarbonyl)piperidinyl-sulfonerhodamine | QSYTM 7 |
| (4-(4'-dimethylaminophenylazo)benzoic acid)polymerase chain reaction | Dabcyl |
|  | PCR |

5. DETAILED DESCRIPTION OF THE INVENTION

The invention stems, in part, from the discovery that having a detectable label directly attached to nucleotide derivatives that are capable of functioning as enzyme substrates offers considerable versatility, both in the experimental protocols that can be performed and in the detection methods (microscopic and non-microscopic) that can be utilized for analysis. Detectable labels (e.g., biotin nucleotides) can be introduced into polynucleotides, which are in the process of being synthesized by cells or crude cell extracts, thus making it possible to detect and/or isolate nascent (growing) polynucleotide chains. Furthermore, enzymes can be used as reagents for introducing probes, such as biotin nucleotides, into highly selective or site-specific locations in polynucleotides.

In one embodiment, a detectable label of the invention can be attached to the 5' or the 3' terminus of an oligo- or polynucleotide, and/or within the sequence. The detection sensitivity depends, for example, on the number of detectable labels attached to the oligonucleotide, primer, or probe. The signal intensity and the detection sensitivity increases with the number of detectable labels attached to the oligonucleotide. Internal labeling may introduce steric hindrance resulting in a lower sensitivity and a destabilizing effect on a hybrid formed between the oligo- or polynucleotide and a target sequence. Therefore, to compromise between hybrid stability, detection sensitivity and cost, in certain embodiments a typical oligo can contain about 3 detectable labels of the invention, one at both termini and one internal, with a minimum of about 15 bases between the moieties. The synthesis of nucleotides containing a detectable label of the invention is achieved as indicated in the examples that follow. Imidazole nucleoside triphosphates containing a detectable label probe attached to the C-5 carbon atom are practical substrates for a wide variety of purified nucleic acid polymerases of both prokaryotic and eukaryotic origin, including but not limited to, DNA polymerase I of E. Coli, bacteriophage T4 DNA polymerase, DNA polymerases α and β from murine (A 9) and human (HeLa) cells, terminal deoxynucleotidyl transferase, and the DNA polymerase of Herpes simplex virus. In addition, detectable label ribonucleoside triphosphates may function as substrates for the RNA polymerases of E. coli and bacteriophage T7. Indeed, detectable labeled RNA probes can be prepared enzymatically from DNA templates using E. Coli or T7 RNA polymerases or by 3' end-labeling methods using RNA ligase with compounds such as biotinyl-pCp. With the availability of antibodies to these analogs, the isolation of nascent transcripts by immunological or affinity procedures is also feasible.

In a modification of the invention, analogs of nucleotides such as, not limited to, dUTP and UTP, that contain a biotin molecule covalently bound to the ring through an allylamine polyethylene glycol linker arm can be synthesized. These biotinyl nucleotides are efficient substrates for a variety of DNA and RNA polymerases in vitro. DNA containing low levels of biotin substitution (50 molecules or less/kilobase) has denaturation, reassociation and hybridization characteristics which are indistinguishable from that of unsubstituted control DNA.

As a non-limiting example, biotinylation provides a label or "tag" that transforms poorly or undetectable molecules into probes that can be recognized by a detection reagent or an affinity capture matrix. Once labeled with biotin, the labeled nucleotide can be used to probe complex protein and nucleic acid blots and arrays. This tagged molecule can then be detected with the appropriate avidin conjugate that has been labeled with a fluorophore, fluorescent microsphere, enzyme, chromophore, magnetic particle or colloidal gold. Biotinylated molecules can also be captured with various forms of immobilized streptavidin, such as streptavidin agarose, or stained for electron microscopy with reactive gold compounds, such as NANOGOLD® (Nanoprobes, Inc., Yaphank, N.Y.) or Alexa Fluor® FluoroNanogold streptavidin 1.4 nm gold clusters (Molecular Probes, Eugene, Oreg.).

5.1 Detectable Labels 5.1.1 Structures of the Compounds and Labels

In one aspect, the invention is directed to a class of compounds that are useful as labels for detection of nucleotide sequences.

A first embodiment of the invention encompasses compounds of formula (I):

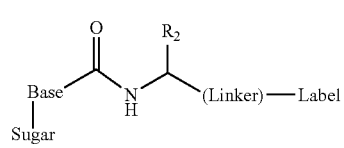

I alone or in combination with a counterion thereof or a stable salt, solvate, clathrate or mixture thereof, wherein:

sugar is a ribose, deoxyribose or a ribose sugar analog;

base is

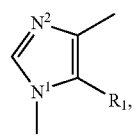

wherein sugar is covalently bonded to $N^1$ of the base;

wherein $R_1$ is —H, —NHC(O)NH$_2$, —NH$_2$, —OH, —O(alkyl), alkyl, CO$_2$H;

wherein $R_2$ is —H, —NH$_2$, —OH, —O(alkyl), alkyl CO$_2$H, —CO$_2$alkyl;

linker is any linker known to those of skill in the art; and label is any label known to those of skill in the art. In one embodiment linker is (alkylO)$_n$, (NH)$_n$, (C(O)NH)$_n$, (NHC(O)NH)$_n$, (NH-alkyl-O-alkyl-NH)$_n$, or (alkyl); wherein n is an integer from 1 to 30. In one embodiment, label is a colorimetric compound, a chemiluminescent compound, a bioluminescent compound, a quencher, a fluorescent compound or a non- or weakly fluorescent compound.

A second embodiment of the invention encompasses a compound of formula II:

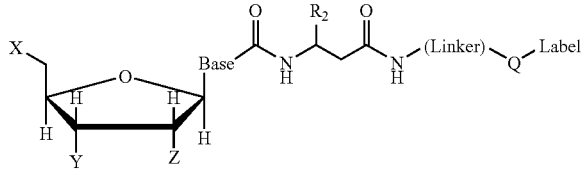

II alone or in combination with a counterion thereof or a stable salt, solvate, clathrate or mixture thereof, wherein:

base is

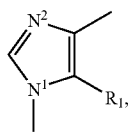

wherein sugar is covalently bonded to $N^1$ of the base;

wherein $R_1$ is —H, —NHC(O)NH$_2$, —NH$_2$, —OH, —O(alkyl), alkyl, CO$_2$H;

wherein $R_2$ is —H, —NH$_2$, —OH, —O(alkyl), alkyl, CO$_2$H, —CO$_2$alkyl;

each of X, Y, and Z is independently —H, —OH, —O(alkyl), —SH, —SR$_4$, —NHR$_4$, —NR$_4$R$_5$,

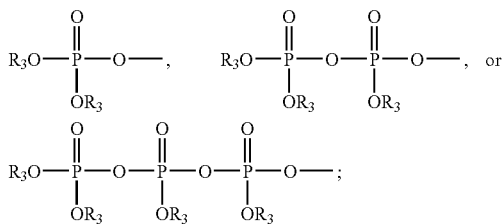

wherein $R_3$ is —H or metal;
$R_4$ is —H or alkyl;
$R_5$ is —H or alkyl;
linker is any linker known to those of skill in the art; and
Q is O, S, or NH; and
label is any label known to those of skill in the art.

In one embodiment of the compound of formula II, at least one of X, Y, and Z is —OH.

In another embodiment of the compound of formula II, each of X, Y, and Z is —OH.

In another embodiment of the compound of formula II, at least one of Y and Z is —OH and X is

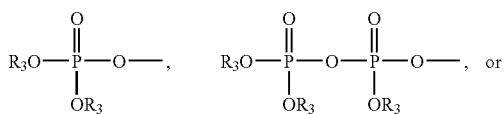

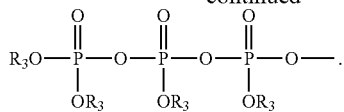

In another embodiment of the compound of formula II, X is

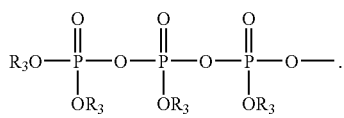

In another embodiment of the compound of formula II, X is

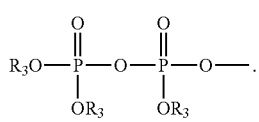

In another embodiment of the compound of formula II, X is

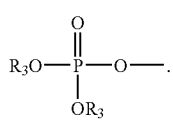

In another embodiment of the compound of formula II, $R_1$ is —H, —NHC(O)NH$_2$, —NH$_2$, —OH, —O-alkyl, alkyl, —COOH.

In another embodiment of the compound of formula II linker is (alkylO)$_n$, (NH)$_n$, (C(O)NH)$_n$, (NHC(O)NH)$_n$, (NH-alkyl-O-alkyl-NH)$_n$, or (alkyl)$_n$; wherein n is an integer from 1 to 30.

In another embodiment of the compound of formula II, the label is a calorimetric compound, a chemiluminescent compound, a bioluminescent compound, a quencher, a fluorescent compound or a non- or weakly fluorescent compound In another embodiment of the compound of formula II, the linker is (CH$_2$CH$_2$O)$_n$, wherein n is an integer between 1 and 10.

In another embodiment of the compound of formula II, the label is biotin, a biotin derivative or a fluorophore.

In another embodiment of the compound of formula II, the fluorophore is fluorescein, tetrachlorofluorescein, hexachlorofluorescein, Cy3, tetramethylrhodamine, Cy3.5, carboxy-x-rhodamine, Texas Red, Cy5, Cy5.5, phycoerythrins, or allophycocynanins.

In another embodiment of the compound of formula II, the label is

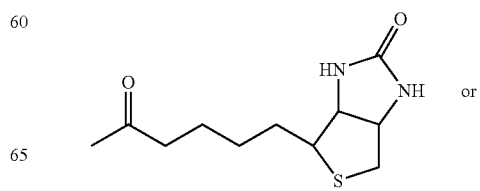

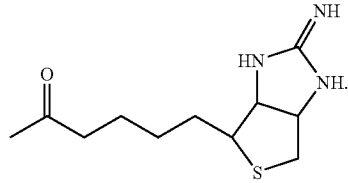
Another embodiment encompasses a compound of formula III:
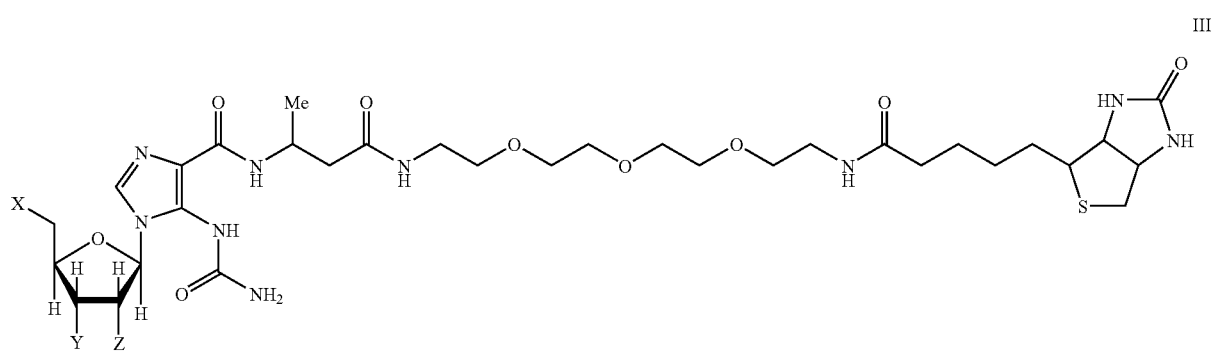
In one embodiment of the compound of formula III, X, Y, and Z are independently H, OH,
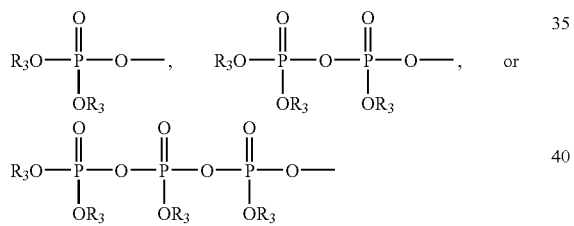
wherein $R_3$ is —H or metal.
In another embodiment of the compound of formula III, the compound is stereomerically pure.
Another embodiment encompasses a compound of formula IV:
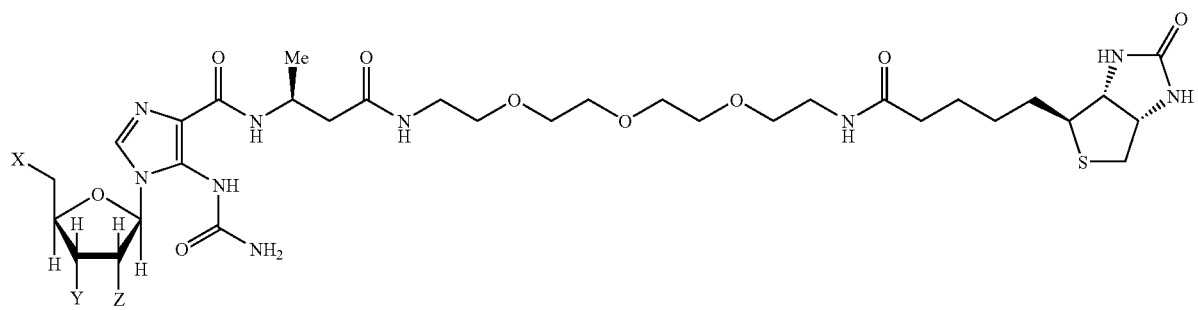

wherein X, Y, and Z are independently H, OH,
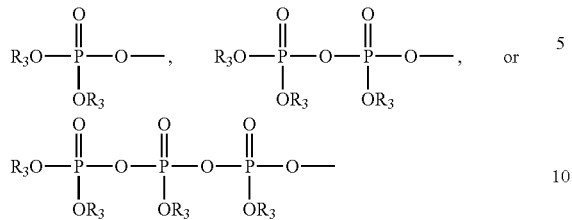
wherein $R_3$ is —H or metal.
Another embodiment encompasses a compound of formula V:
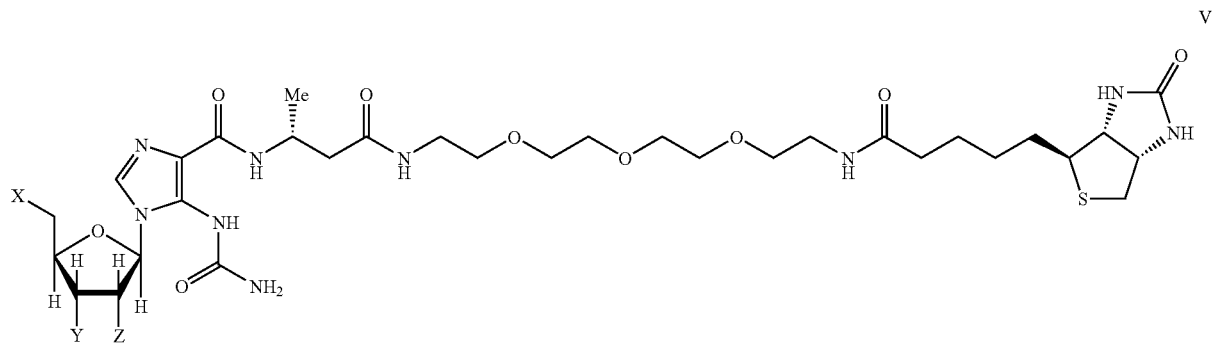
wherein X, Y, and Z are independently H, OH,
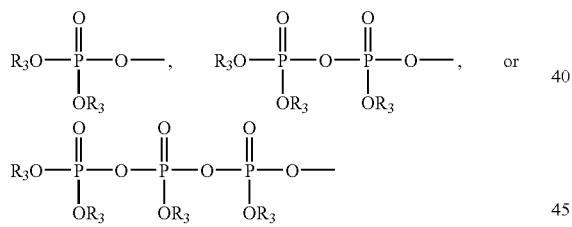
wherein $R_3$ is —H or metal.
Another embodiment encompasses a compound of formula VI:
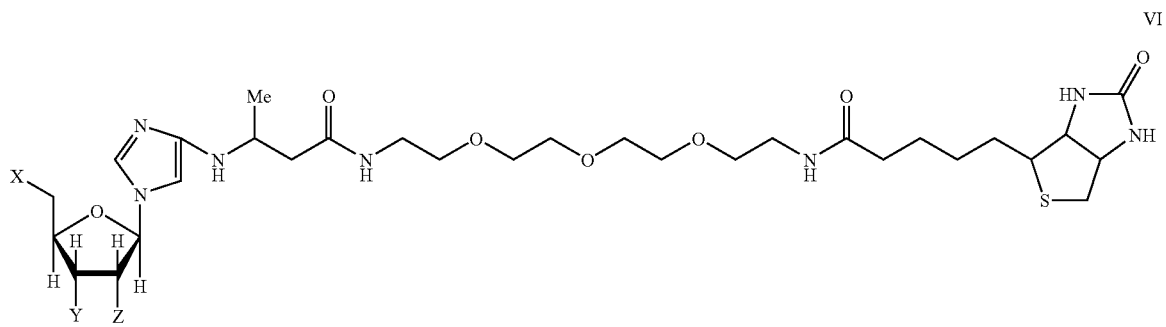

wherein X, Y, and Z are independently H, OH,
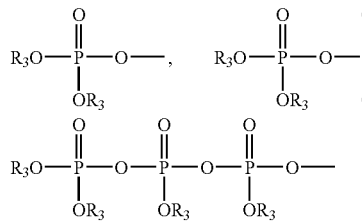
or
wherein $R_3$ is H or metal.
In another embodiment the compound is stereomerically pure.
Another embodiment encompasses a compound of formula VII:
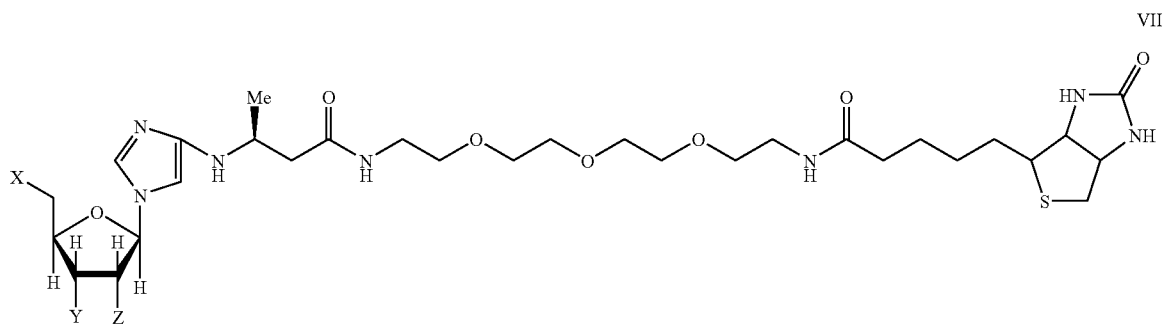
VII
wherein X, Y, and Z are independently H, OH,
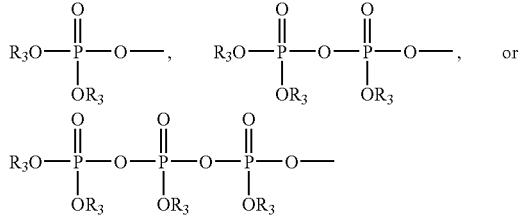
or
wherein $R_3$ is H or metal.
Another embodiment encompasses a compound of formula VIII:
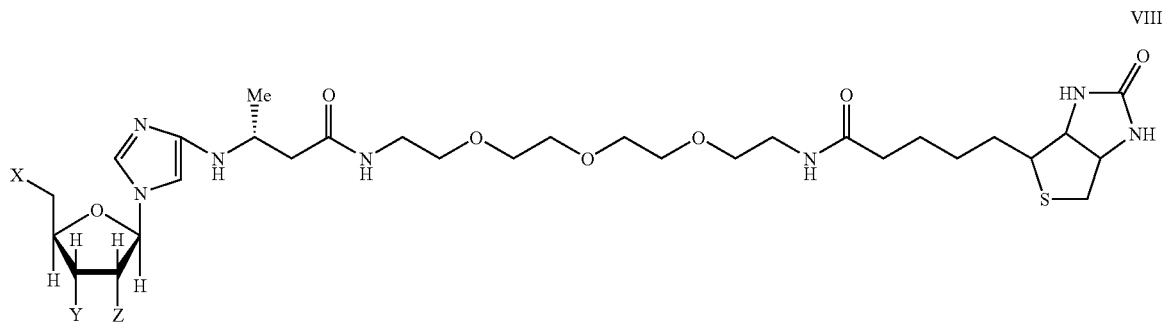
VIII wherein X, Y, and Z are independently H, OH,
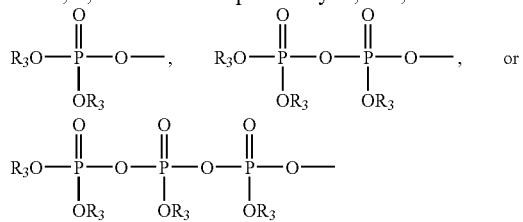
or
wherein $R_3$ is H or metal.
Another embodiment encompasses a compound of formula IX:
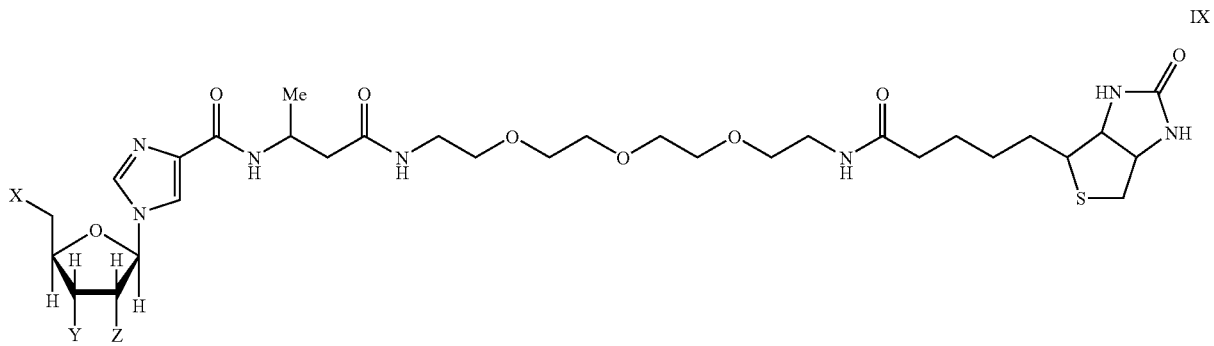
wherein X, Y, and Z are independently H, OH,
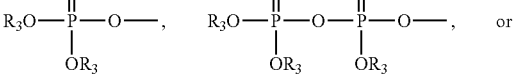
or
wherein $R_3$ is H or metal.
Another embodiment encompasses a compound of formula X:
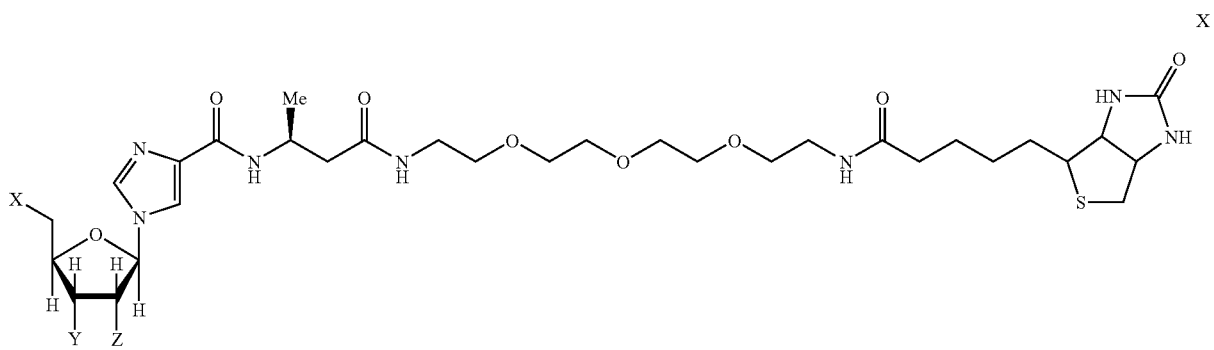

wherein X, Y, and Z are independently H, OH,
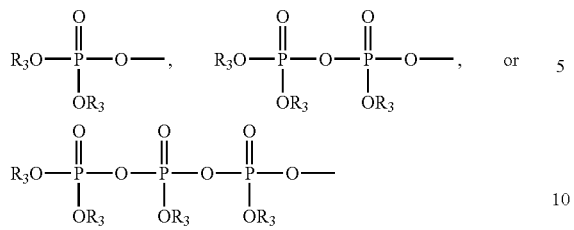 or
wherein $R_3$ is H or metal.
Another embodiment encompasses a compound of formula XI:
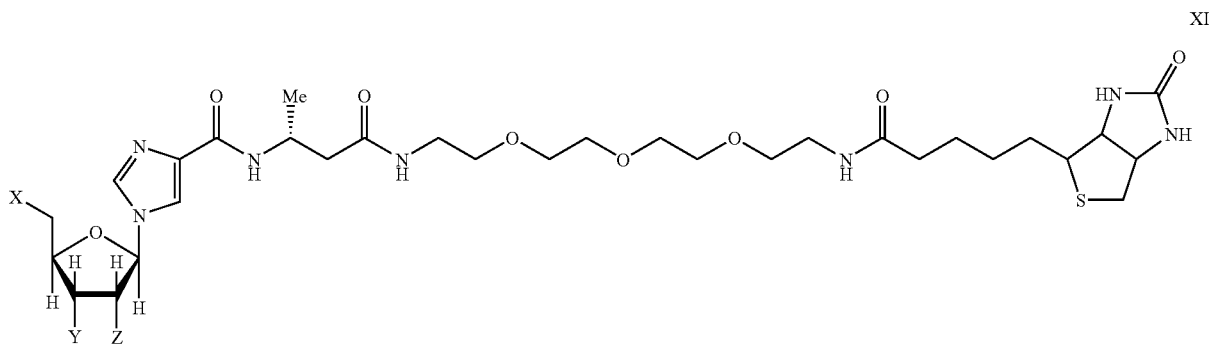
wherein X, Y, and Z are independently H, OH,
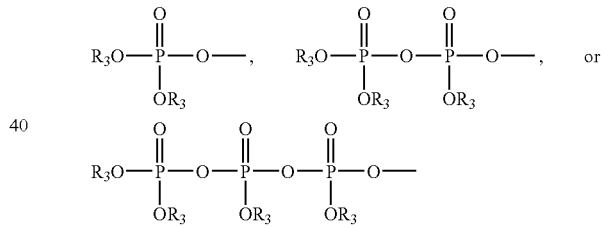 or
wherein $R_3$ is H or metal.
Another embodiment encompasses a compound of formula XII:
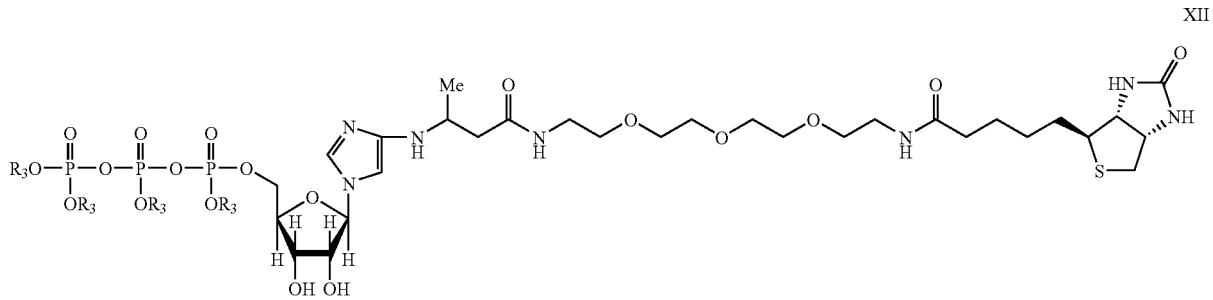

Another embodiment encompasses a compound of formula XIII:
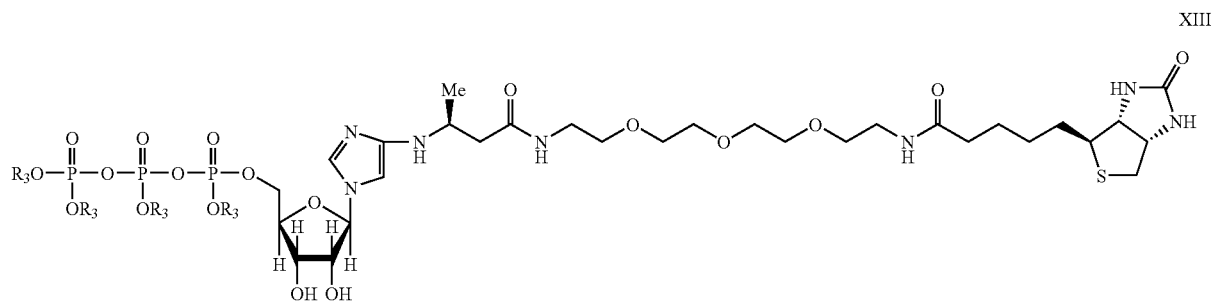
wherein $R_3$ is H or metal.
Another embodiment encompasses a compound of formula XIV:
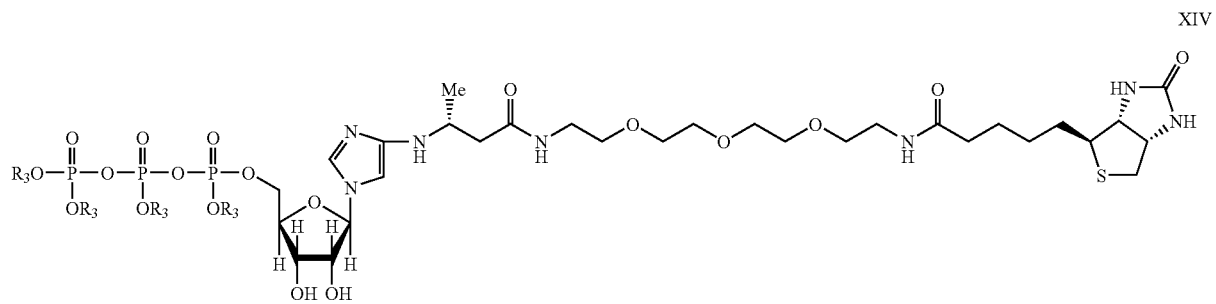
wherein $R_3$ is H or metal.
Another embodiment encompasses a compound of formula XV:
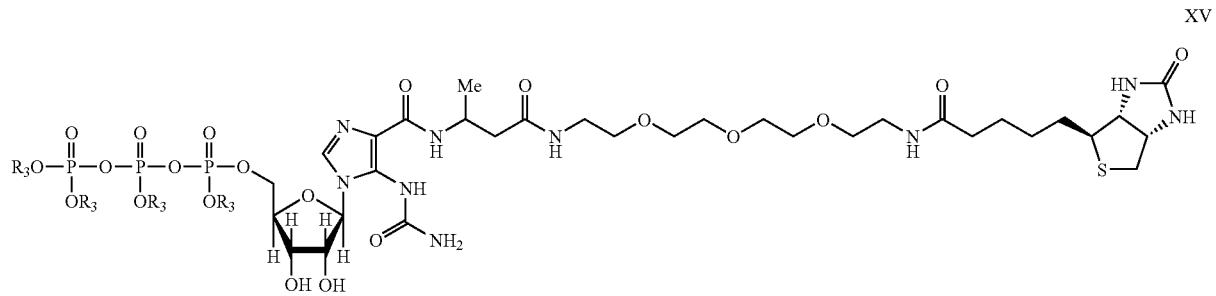
wherein $R_3$ is H or metal.

Another embodiment encompasses a compound of formula XVI:
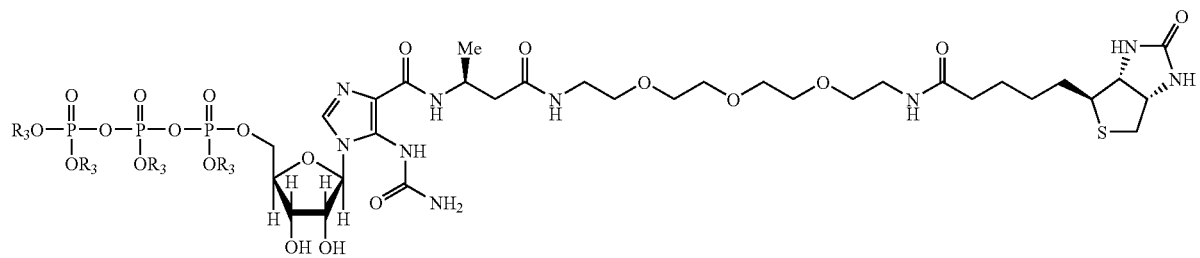
XVI
wherein R₃ is H or metal.
Another embodiment encompasses a compound of formula XVII:
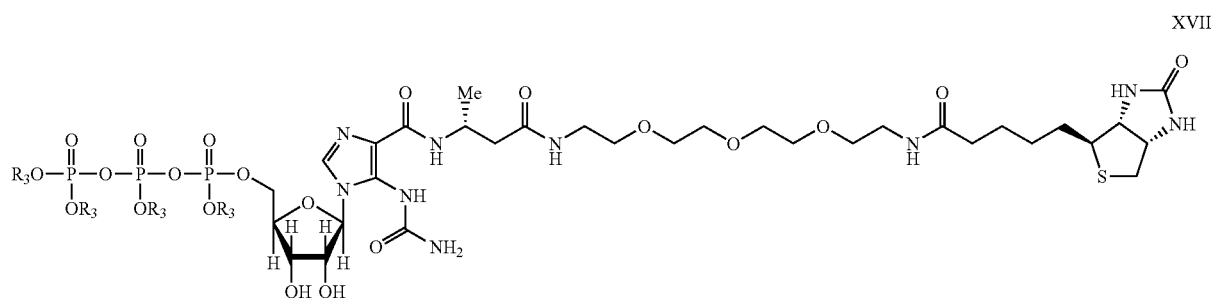
XVII
wherein R₃ is H or metal.
Another embodiment encompasses a compound of formula XVIII:
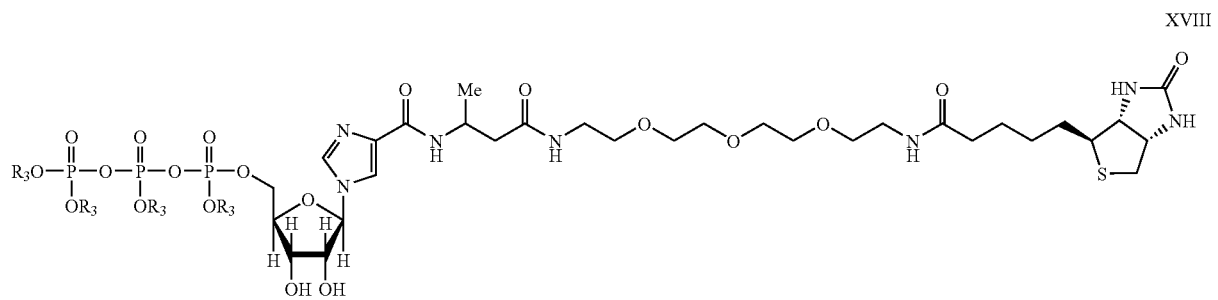
XVIII
wherein R₃ is H or metal.

Another embodiment encompasses a compound of formula XIX:

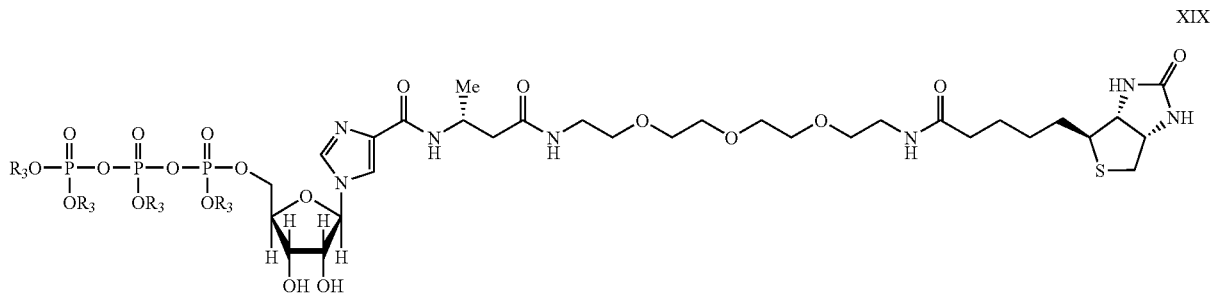

wherein $R_3$ is H or metal.

Another embodiment encompasses a compound of formula XX:

wherein $R_3$ is H or metal.

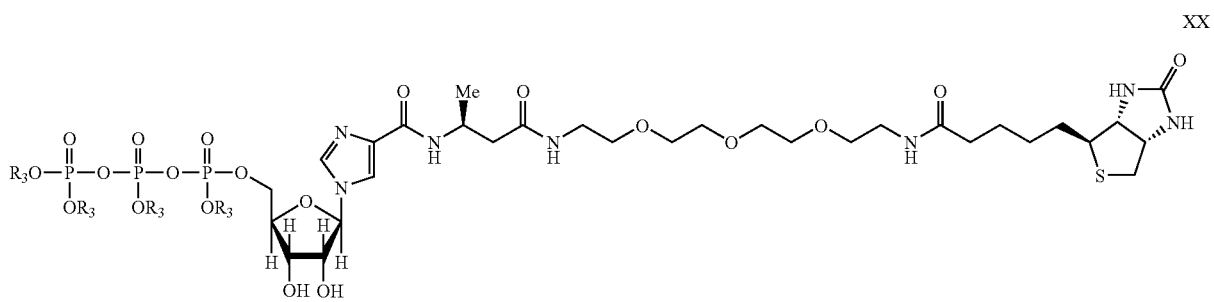

wherein $R_3$ is H or metal.

Another embodiment encompasses an oligonucleotide comprising a detectable label of formula (XXI):

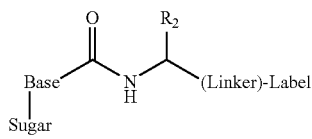

alone or in combination with a counterion thereof or a stable salt, solvate, clathrate or mixture thereof, wherein:
sugar is a ribose, deoxyribose or a ribose sugar analog;
base is

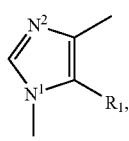

wherein sugar is covalently bonded to $N^1$ of the base;
wherein $R_1$ is —NHC(O)NH$_2$, —H, —NH$_2$, —OH, —O(alkyl), alkyl, or CO$_2$H;
wherein $R_2$ is —H or alkyl,
linker is (CH$_2$CH$_2$O)$_n$, (CH$_2$O)$_n$ or (CH$_2$)$_n$;

wherein n is an integer from 1 to 30; and
label is a colorimetric, chemiluminescent, bioluminescent, a fluorescent compound, or a non- or weakly fluorescent compound.

Another embodiment encompasses an oligonucleotide comprising a detectable label of formula XXII:

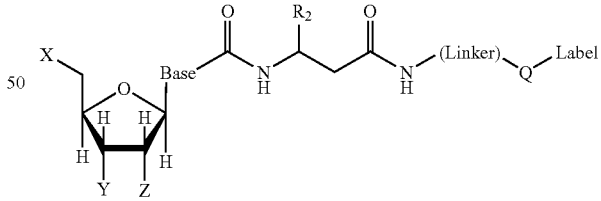

alone or in combination with a counterion thereof or a stable salt, solvate, clathrate or mixture thereof, wherein:
base is

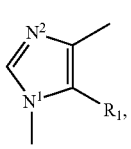

wherein sugar is covalently bonded to $N^1$ of the base;
wherein $R_1$ is —NHC(O)NH$_2$, —H, —NH$_2$, —OH, —O(alkyl), alkyl, or CO$_2$H;
wherein $R_2$ is —H or alkyl;
each of X, Y, and Z is independently —H, —OH, —O-alkyl, —SH, —SR$_4$, —NHR$_4$, —NR$_4$R$_5$,

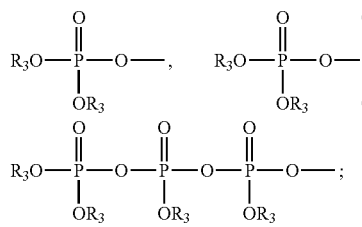

wherein $R_3$ is —H or metal;
$R_4$ is —H or alkyl;
$R_5$ is —H or alkyl;
linker is (CH$_2$CH$_2$O)$_n$, (CH$_2$O)$_n$ or (CH$_2$)$_n$;
wherein n is an integer from 1 to 30;
Q is O, S, or NH; and
label is a colorimetric, chemiluminescent, bioluminescent, a fluorescent compound, or a non- or weakly fluorescent compound.

In one embodiment at least one of X, Y, and Z is —OH.
In another embodiment each of X, Y, and Z is —OH.
In another embodiment at least one of Y and Z is —OH and X is

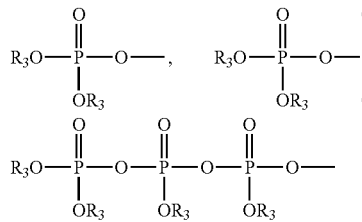

wherein $R_3$ is —H or metal.
In another embodiment X is

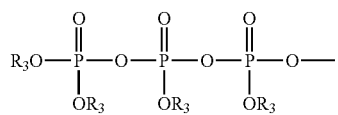

wherein $R_3$ is —H or metal.
In another embodiment X is

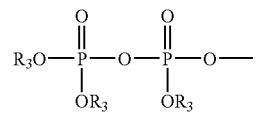

wherein $R_3$ is —H or metal.
In another embodiment X is

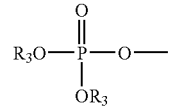

wherein $R_3$ is —H or metal.
In another embodiment $R_1$ is —NHC(O)NH$_2$.
In another embodiment linker is (CH$_2$CH$_2$O)$_n$, wherein n is an integer from 1 to 10.
In another embodiment label is biotin, a biotin derivative or a fluorophore.
In another embodiment the fluorophore is fluorescein, tetrachlorofluorescein, hexachlorofluorescein, Cy3, tetramethylrhodamine, Cy3.5, carboxy-x-rhodamine, Texas Red, Cy5, Cy5.5, phycoerythrins, or allophycocyanins.
In another embodiment the label is

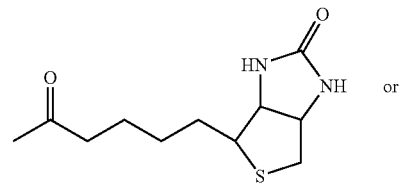

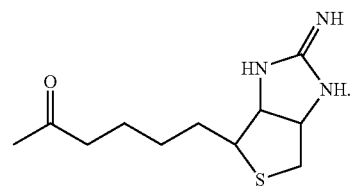

Another embodiment encompasses a detectable label of formula XXIII:

XXIII

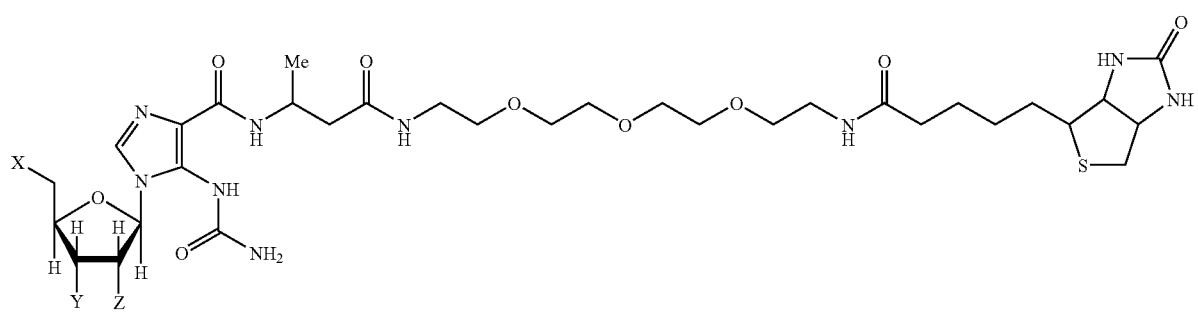

wherein X, Y, and Z are independently H, OH,

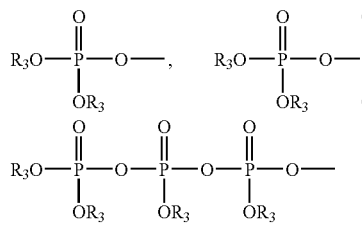

or wherein $R_3$ is —H or metal.

In another embodiment the detectable label is stereomerically pure.

Another embodiment encompasses a detectable label of formula XXIV:

wherein X, Y, and Z are independently H, OH,

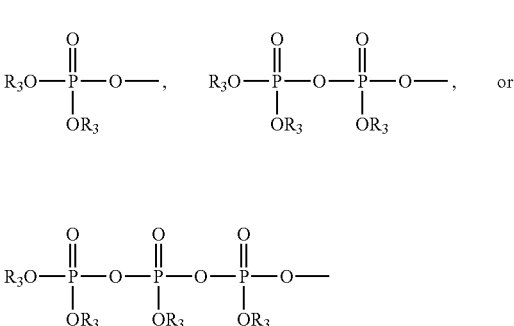

or wherein $R_3$ is —H or metal.

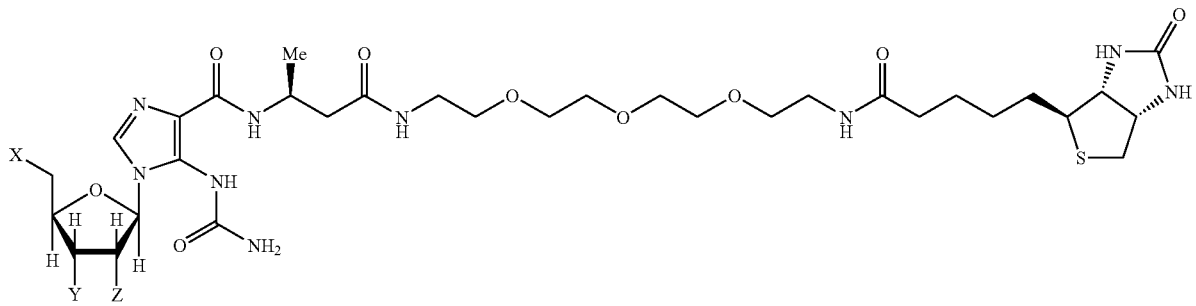

XXIV

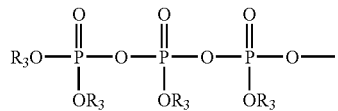

wherein X, Y, and Z are independently H, OH,

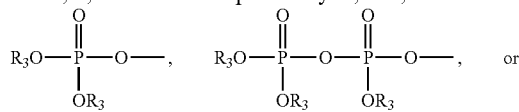

or wherein $R_3$ is —H or metal.

Another embodiment encompasses a detectable label of formula XXV:

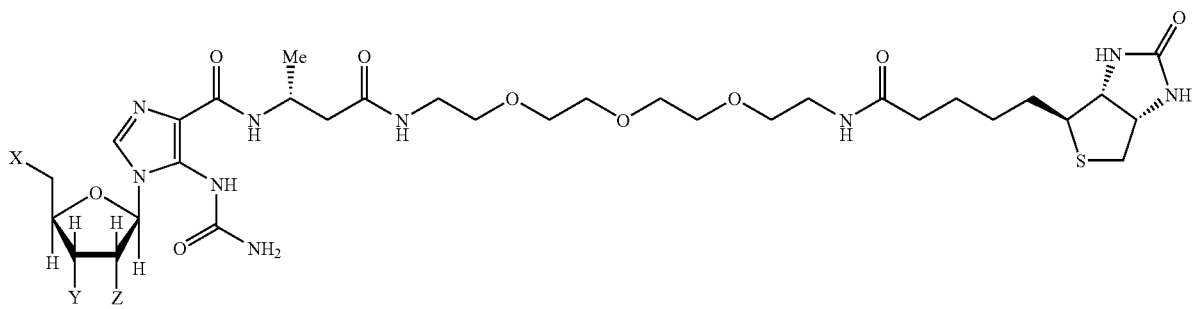

XXV

Another embodiment encompasses a detectable label of formula XXVI:
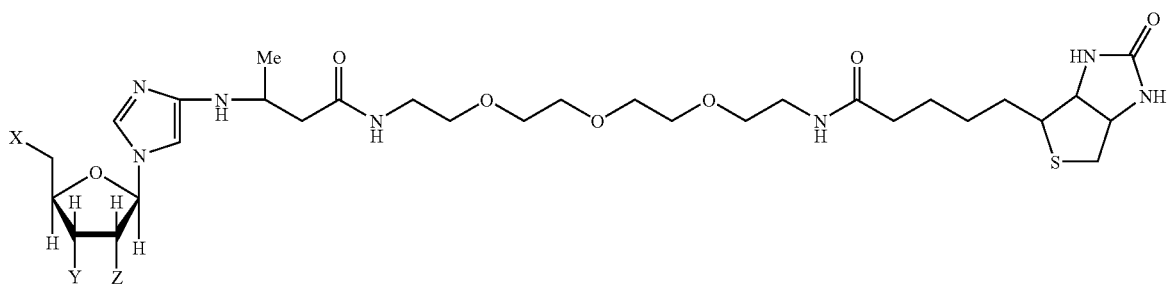
wherein X, Y, and Z are independently H, OH,
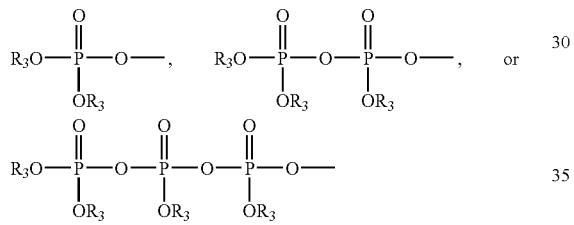
wherein $R_3$ is —H or metal.
In another embodiment the detectable label is stereomerically pure.
Another embodiment encompasses a detectable label of formula:
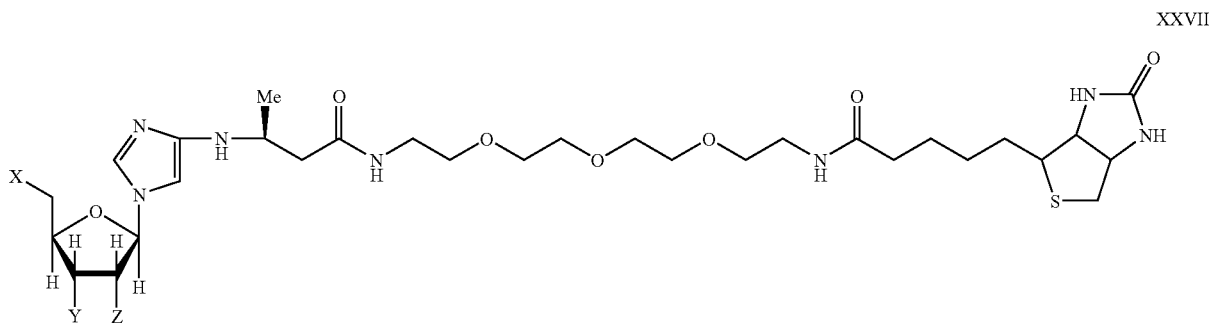

wherein X, Y, and Z are independently H, OH,
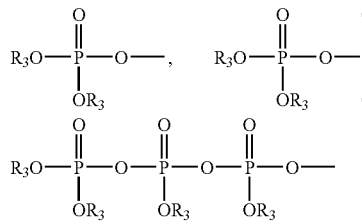
wherein $R_3$ is —H or metal.
Another embodiment encompasses a detectable label of formula XXVIII:
wherein X, Y, and Z are independently H, OH,
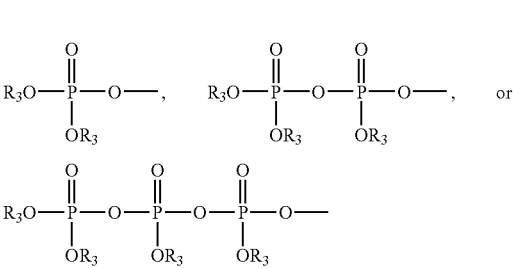
wherein $R_3$ is —H or metal.
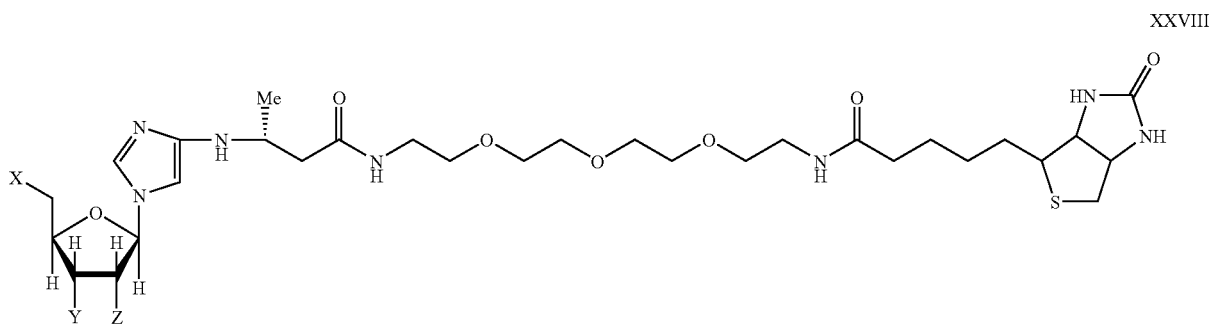
XXVIII
wherein X, Y, and Z are independently H, OH,
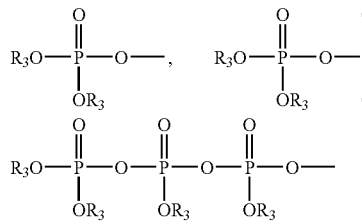
wherein $R_3$ is —H or metal.
Another embodiment encompasses a detectable label of formula XXIX:
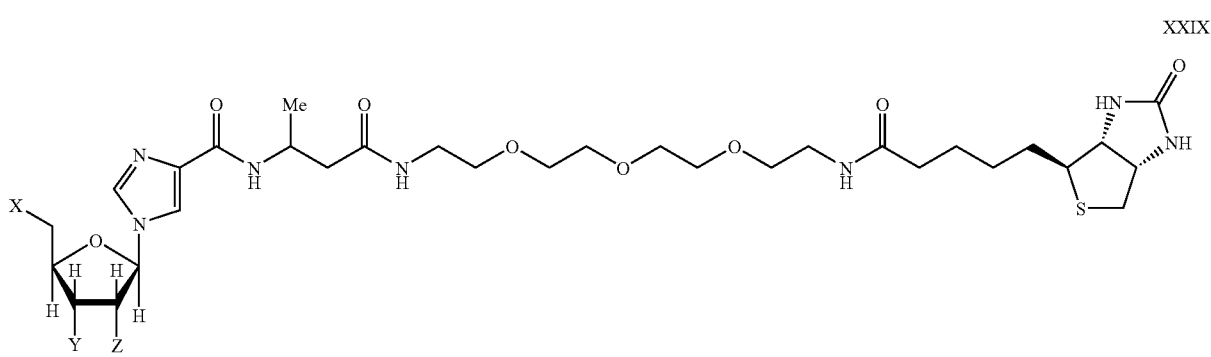
XXIX In another embodiment the detectable label is stereomerically pure.
Another embodiment encompasses a detectable label of formula XXX:
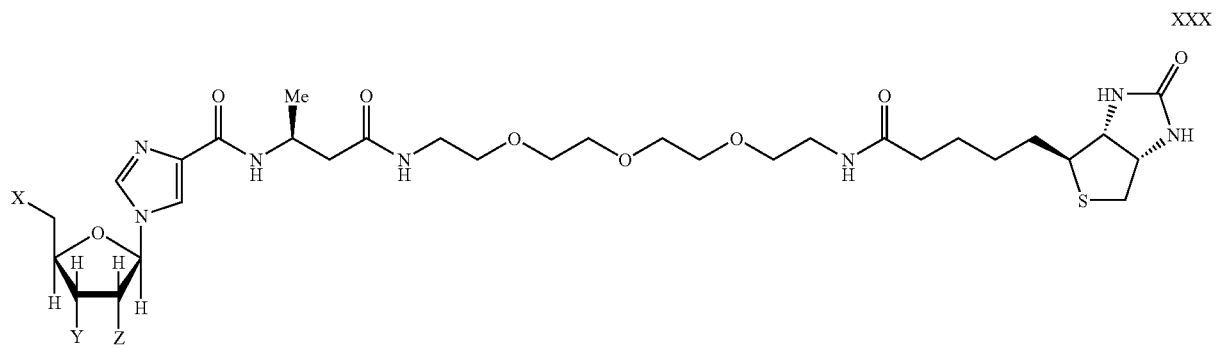
wherein X, Y, and Z are independently H, OH,
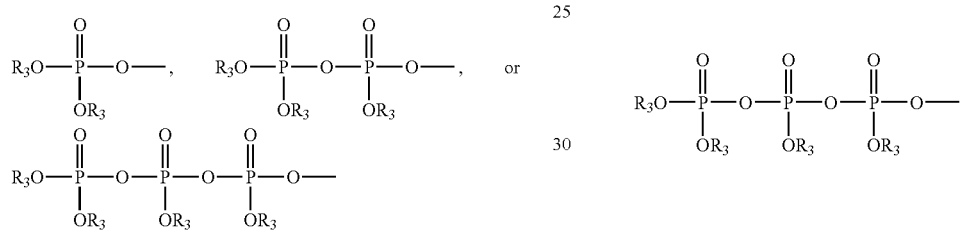
wherein $R_3$ is —H or metal.
Another embodiment encompasses a detectable label of formula XXXI:
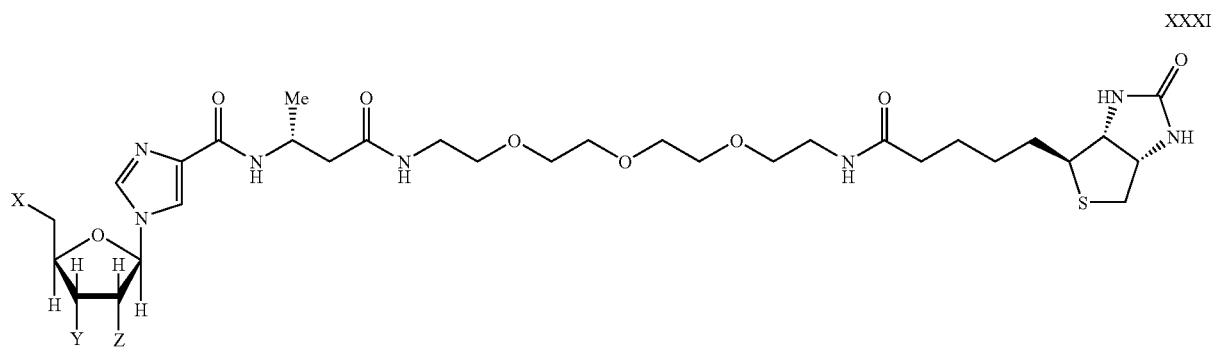
wherein X, Y, and Z are independently H, OH,
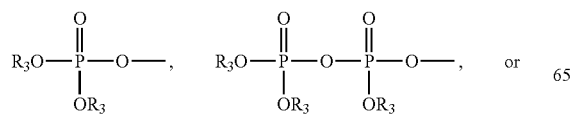

Another embodiment encompasses a detectable label of formula XXXII:
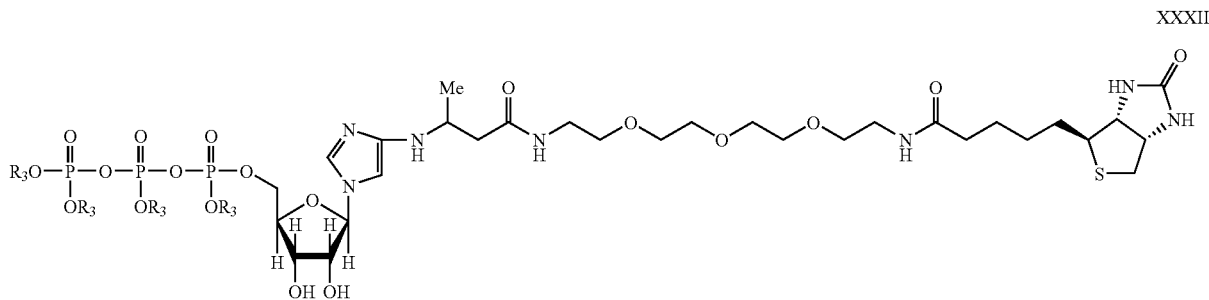
Wherein R₃ is H or metal.
Another embodiment encompasses a detectable label of formula XXXIII:
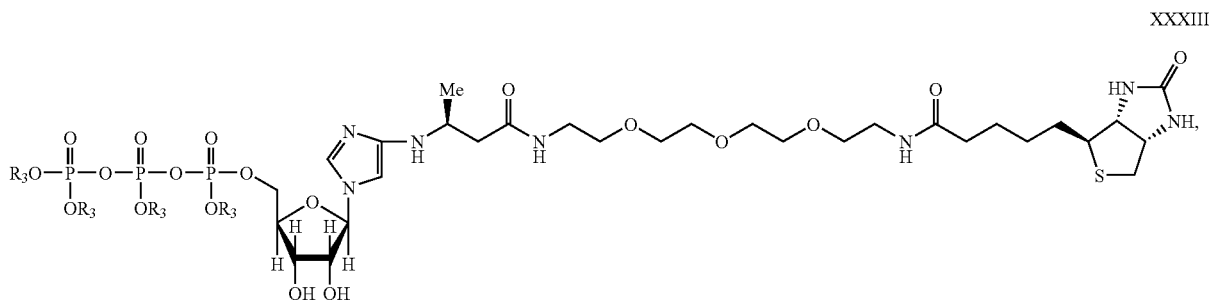
wherein R₃ is H or metal.
Another embodiment encompasses a detectable label of formula XXXIV:
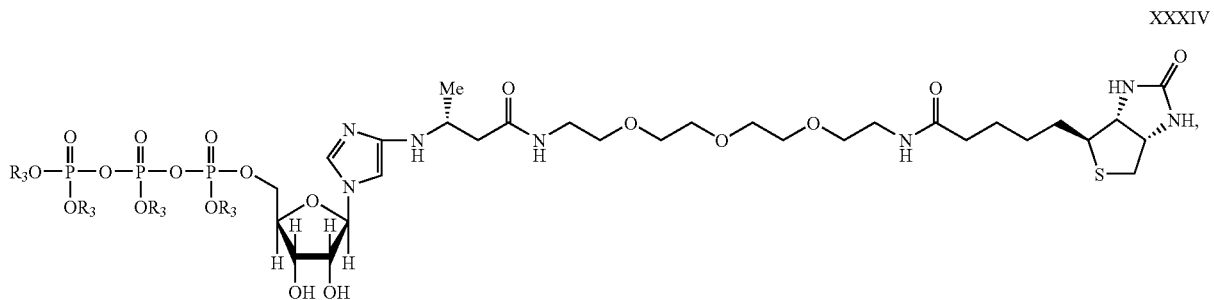
wherein R₃ is H or metal.

Another embodiment encompasses a detectable label of formula XXXV:
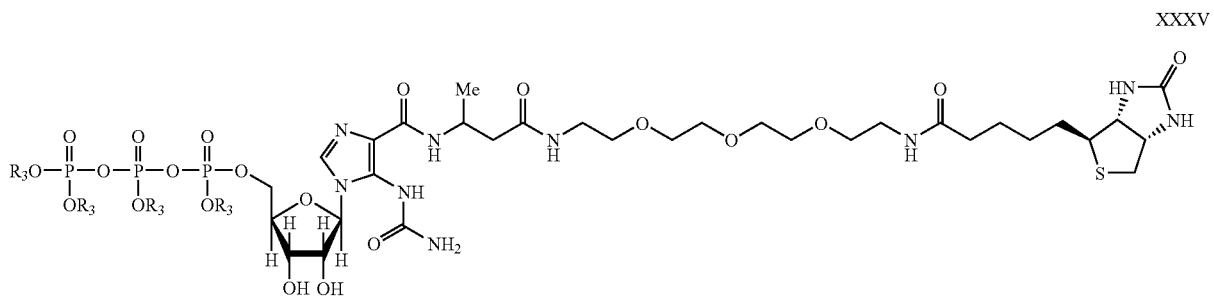
XXXV
wherein $R_3$ is H or metal.
Another embodiment encompasses a detectable label of formula XXXVI:
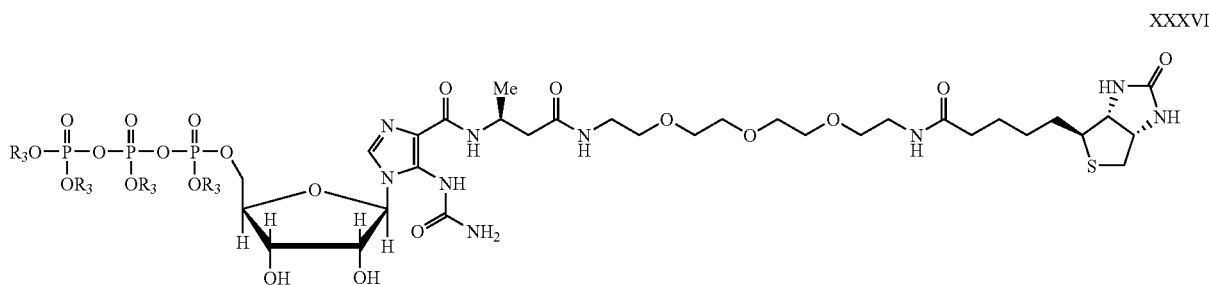
XXXVI
wherein $R_3$ is H or metal.
Another embodiment encompasses a detectable label of formula XXXVII:
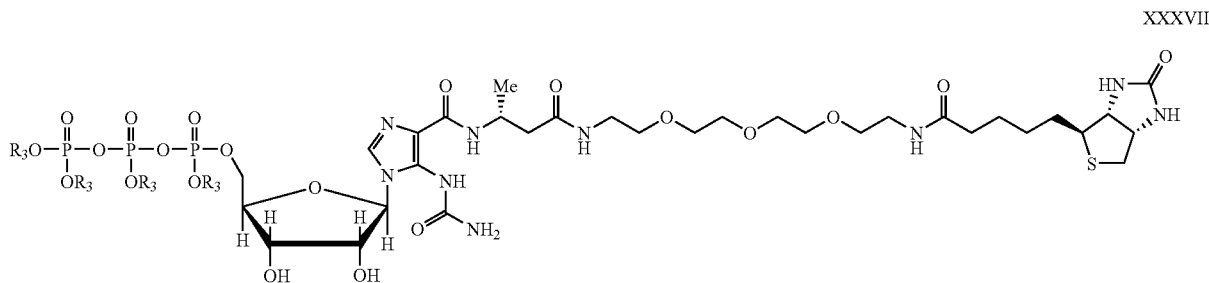
XXXVII
wherein $R_3$ is H or metal.

Another embodiment encompasses a detectable label of formula XXXVIII:

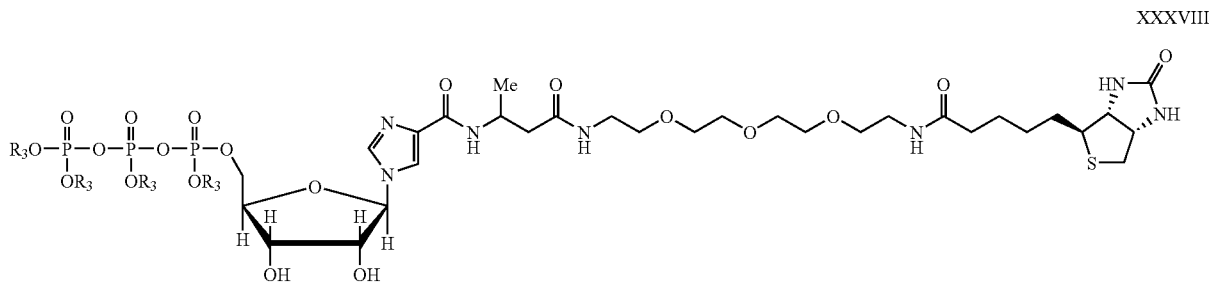

XXXVIII wherein $R_3$ is H or metal.

Another embodiment encompasses a detectable label of formula XXXIX:

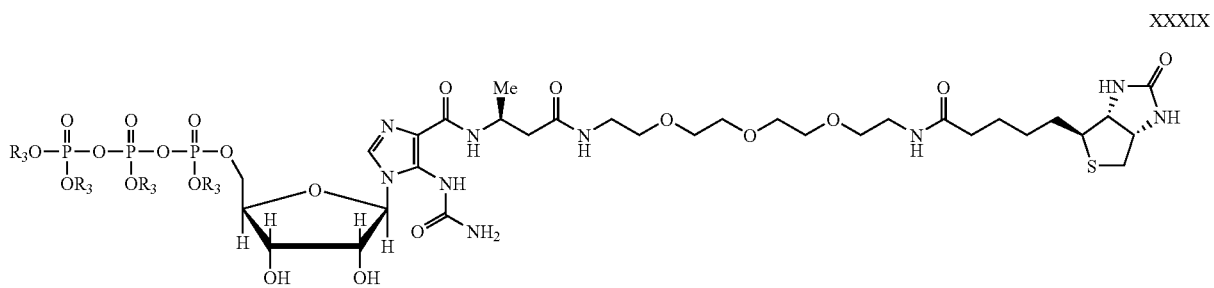

XXXIX wherein $R_3$ is H or metal.

Another embodiment encompasses a detectable label of formula XXXX:

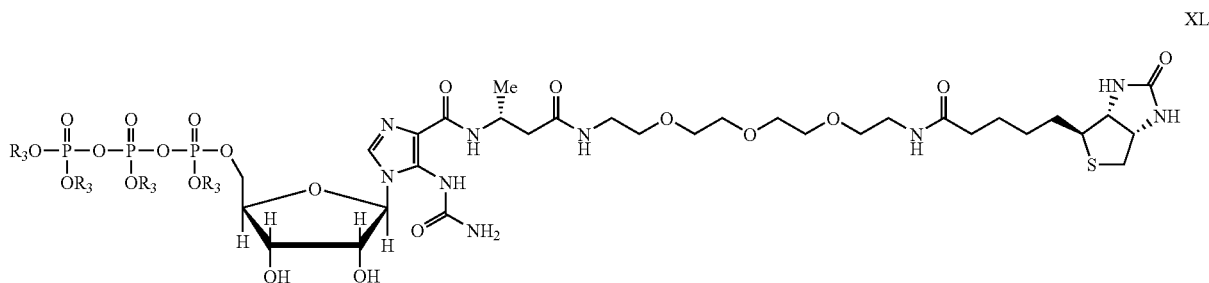

XL wherein $R_3$ is H or metal.

5.1.2 Detectable Label Base

Compounds of formula I described herein can be used as detectable labels. Imidazole compounds are in principle compatible as bases in the detectable labels of formula I. Thus, the invention encompasses bases including, but not limited to, imidazoles and substituted imidazoles. Preferred bases include, but are not limited to:

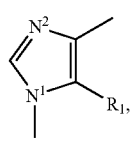

wherein the sugar of the nucleoside or nucleotide is covalently bonded to $N^1$ of the base; and wherein R₁ is —NHC(O)NH₂, —H, —NH₂, —OH, —O(alkyl), alkyl, or CO₂H.

5.1.3 Linking Groups or Linkers

The invention comprises conjugating or linking a nucleoside, nucleotide, or a nucleoside or nucleotide analogs to compounds of formula I. The compounds of formula I are conjugated via the linking group by a variety of means, including ionic attraction or covalent attachment. Preferably, the compounds are linked via covalent attachment. The linking groups or linkers are capable of reacting with a "complementary functionality" of a reagent, e.g., a nucleoside or nucleotide or nucleic acid, and forming a "linkage" that connects the compound to the label. The linker can be any linker known to those of skill in the art. Preferred linking groups include but are not limited to, $(CH_2CH_2O)_n$, $(CH_2O)_n$, or $(CH_2)_n$; wherein n is an integer from about 1 to about 30, preferably n is an integer from about 2 to about 20, more preferably n is an integer from about 3 to about 10. Optionally, the linker is a covalent bond (i.e., label may be bonded to the base by a covalent bond).

5.1.4 Labels

The label can be any detectable label known to those of skill in the art. Labels that can be used with compounds of formula I include biotin, biotin derivatives and any fluorophore. In certain embodiments, labels containing biotin or a fluorescent reporter may be used. Flourescent reporters may be selected from xanthene dyes, including fluoresceins, and rhodamine dyes. Many suitable forms of these compounds are commercially available having various substituents on their xanthene rings that can be used as a site for bonding or as the bonding functionality for attachment to a reagent, preferably an oligonucleotide. Another group of fluorescent labels are the naphthylamines and their derivatives, having an amino group in the alpha or beta position. Included among such naphthylamino compounds are 1-dimethylaminonaphthyl-5-sulfonate, 1-anilino-8-naphthalene sulfonate and 2-p-toluidinyl-6-naphthalene sulfonate. Other labels include, but are not limited to, coumarins, such as 3-phenyl-7-isocyanatocoumarin; acridines, such as 9-isothiocyanatoacridine and acridine orange; N-(p-(2-benzoxazolyl)phenyl)-maleimide; cyanines; BODIPY® dyes (Molecular Probes, Eugene, Oreg.); benzoxadiazoles; stilbenes; pyrenes; and the like.

Preferably, labels are selected from biotin, fluorescein and rhodamine dyes. More preferably the label is biotin. These labels and appropriate linking methodologies for attachment to oligonucleotides are described elsewhere (Khanna et al. U.S. Pat. No. 4,439,356; Marshall, 1975, *Histochemical J.*, 7:299-303; Menchen et al., U.S. Pat. No. 5,188,934; Menchen et al., European Patent Application No. 87310256.0; Bergot et al., International Application PCT/U590/05565; and Barone et al., 2001, *Nucleosides, Nucleotides, and Nucleic Acids*, 20(4-7): 1141-1145).

In certain specific embodiments, the label is biotin, fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N'N'tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl)aminonaphthalene 1 sulfonic acid (EDANS), tetrachlorofluorescein (TET), indodicarbocyanine 3 (Cy3), indodicarbocyanine 5 (Cy 5), indodicarbocyanine 5.5 (Cy 5.5), 3-(-carboxy pentyl)-3'-ethyl-5,5'-dimethyloxacarbo-cyanine (CyA), or 1H,5H,11H,15H-xantheno[2,3,4 ij:5, 6,7-i'j']diquinolizin-18-ium, 9-[2(or 4)-[[[6[2,5-dioxo-1-pyrrolidinyl)oxy]-6-oxohexyl]amino]sulfonyl]-4(or 2)-sulfophenyl]2,3,6,7,12,13,16,17-octahydro-, inner salt (TR or Texas Red). Representative fluorophores include:

| Fluorophore | Emission Max |
|---|---|
| Fluorescein | 520 nm |
| Tetrachlorofluorescein (TET) | 536 nm |
| Hexachlorofluorescein (HEX) | 556 nm |
| Cy3 | 570 nm |
| Tetramethylrhodamine (Tamra) | 580 nm |
| Cy3.5 | 596 nm |
| Carboxy-x-rhodamine (Rox) | 605 nm |
| Texas Red | 610 nm |
| Cy5 | 667 nm |
| Cy5.5 | 694 nm |

5.1.5 Sugars

The sugars that are generally compatible with compounds of formula I include, ribose and ribose analogs of formula:

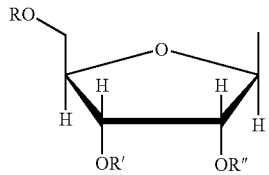

wherein R, R', and R" are independently H, metal, or a mono-, di-, or triphosphate.

5.2 Purification of Detectably Labeled Oligonucleotides

Oligonucleotides containing a compound of formula I can be purified by any method known to one of ordinary skill in the art. In one nonlimiting embodiment, the oligonucleotides are purified by reverse phase HPLC. Briefly, the sample containing the oligonucleotide is loaded on a Hamilton PRP-1 column (1.0 cm×25 cm) and eluted with a linear 5% to 50% acetonitrile gradient over 40 minutes. HPLC fractions corresponding to the fluorescent labeled oligonucleotide species are collected, pooled, and lyophilized. Following lyophilization, the oligonucleotide samples can be dissolved in water and precipitated, for example with lithium perchlorate, followed by centrifugation, e.g., at 10,000 g for 10 minutes. The resulting pellet can then be washed with 10% aqueous acetone. This method yields "standard purity" single reverse phase HPLC (RP-HPLC) oligonucleotides.

The oligonucleotides optionally can be repurified by ion exchange HPLC to yield "high purity" dual reverse phase plus ion exchange HPLC (IE+RP HPLC) purified oligonucleotides. In one embodiment, the oligonucleotides are repurified by loading them on a 5×10 Source column (Amersham Pharmacia Biotech, Piscataway, N.J.) and eluted using a linear 0% to 50% gradient of 1 M LiCl, 0.1 M TRIS buffer pH 8.0. HPLC peaks corresponding to the oligonucleotide species are collected, pooled, precipitated with lithium perchlorate, and lyophilized.

Compound and/or oligonucleotide identities can be verified after synthesis and purification by mass spectroscopy, for example using a Voyager DE BioSpectrometry workstation (PE BioSystems, Framingham, Mass.).

5.3 Detection of Detectable Labels

The detectable label can be detected by any means known to those of skill in the art to be suitable for detection of the label without limitations. For instance, certain modified nucleotides, oligonucleotides, and polynucleotides of the invention may be detected by contacting the compounds with polypeptides (e.g., avidin or an antibody) which are capable of forming complexes under suitable conditions, provided that the polypeptides include one or more moieties which can be detected when the complex or complexes is or are formed, generally by means of conventional detection techniques. Other detectable labels can be detected, for example, by spectroscopic techniques.

5.3.1 Avidin

One polypeptide detector for a biotin-labeled detectable label of the invention is avidin. If avidin is coupled to potentially demonstrable indicator molecules, (e.g., fluorescent dyes such as, but not limited to, fluorescein or rhodamine), electron dense reagents (e.g., ferritin, hemocyanin, or colloidal gold), or enzymes capable of depositing insoluble reaction products (e.g., peroxidase or alkaline phosphatase) the presence, location and/or quantity of the probe can be established.

Avidin-biotin techniques can be used in flow cytometry and light, electron and fluorescence microscopy, as well as with solution based methods such as enzyme linked immunosorbent assays (ELISAs). In addition, avidin-biotin and antibody-hapten techniques are frequently combined for simultaneous, multicolor detection of multiple targets in a complex solution, cell or tissue sample. Furthermore, by judicious choice of detection reagents and sandwich protocols, these techniques can be employed to amplify the signal from low-abundance analytes. For example, the bridging method is a common immunohistochemical technique for signal amplification and improved tissue penetration in which avidin or streptavidin serves as a bridge between two biotinylated molecules.

Avidin has, unfortunately, one property that makes it less desirable as a biotin indicator protein when used in conjunction with nucleic acids or chromatin material. It has been reported that avidin binds tightly to condensed chromatin or to subcellular fractions that contain large amounts of nucleic acid in a manner which is independent of its biotin-binding property (Heggeness, 1978, *Stain Technol.*, 52: 165; Heggeness et al., 1977, *J. Cell. Biol.*, 73: 783; and Bayer et al., 1980, *Methods of Biochemical Analysis*, 26: 1).

5.3.2 Streptavidin

Another probe for biotin-containing nucleotides and derivatives is streptavidin, an avidin-like protein synthesized by the soil organism *Streptomyces avidinii*. Its preparation and purification is described in Hoffman, et al., 1980, *Proc. Natl. Acad. Sci.*, 77: 4666, which is incorporated herein by reference. Streptavidin has a much lower pI (5.0) than avidin, is non-glycosylated, and shows much lower non-specific binding to DNA than avidin, and therefore offers potential advantages in applications involving nucleic acid detection methodology.

The protein streptavidin is a potential alternative to antibiotin IgG as a vehicle to specifically direct a coupled visualization system (e.g., fluorescent probes (see § 4.6.1.1. below) or histochemical reagents (see § 4.3.3. below) to the site of the hybridized biotin-containing polynucleotide. One of streptavidin's advantages over anti biotin IgG is that its affinity for biotin is $K_{assn}=10^{15}$ whereas association constants for haptene IgG interactions are $10^7$ to $10^{10}$. The fast reaction rate and extreme affinity mean that the time required to localize the biotinized probe will be minutes with streptavidin versus hours with immunologic reagents.

The analysis of protein from tissue samples using a biotin streptavidin detection system is well known in the art as exemplified by western blot detection using the Bio Rad Amplified Alkaline Phosphatase Immun-Blot Detection (BioRad Laboratories, Hercules, Calif.). This detection format uses a biotinylated secondary antibody with the amplification of streptavidin. Then biotinylated alkaline phosphatase completes the sandwich and color developing reagent (e.g., 5-bromo-4-chloro-indoyl phosphate and nitroblue tetrazolium) is added. This forms a purple precipitate at any point of binding of the biotinylated alkaline phosphatase.

5.3.3. Monospecific Rabbit IgG Antibiotin Immunoglobulin

A protein for biotin like probe detection is monospecific rabbit IgG, antibiotin immunoglobulin. This compound may be prepared by immunizing rabbits with bovine serum albumin-conjugated biotin, followed by purification by affinity chromatography (Berger, 1979, *Methods in Enzymology*, 62: 319). The anti-biotin antibodies have proven extremely useful in detecting specific polynucleotide sequences on chromosomes by in situ hybridization since little, if any, non specific binding of the antibody to chromatin material occurs.

5.3.4 Immunological and Histochemical Methods

Immunological and histochemical methods for the detection of biotin have shown that the basic approach is useable for a rapid method of gene mapping in situ hybridization and non-radioactive procedures for detecting specific nucleic acid sequences by blotting hybridization methods. Use may be made of this technology in development of new clinical diagnostic procedures.

Using this approach, it is possible to determine the presence of a specific deoxyribonucleic or ribonucleic acid molecule, particularly such a molecule derived from a living organism (e.g., bacteria, fungus, virus, yeast, or mammal). This in turn permits diagnosis of nucleic acid containing etiological agents in a patient or other subject.

Moreover, it provides a method for screening bacteria to determine antibiotic resistance. Thus, for example, penicillin resistance in *Streptococcus pyogenes* or *Neisseris meningitidis*, tetracycline resistance in *Staphylococcus aureus, Candida albicans, Pseudomonas aeruqinosa, Streptococcus pyogenes*, or *Neisseria gonorrhoeae*; and aminoglycoside resistance in *Mycobacterium tuberculosis* can be determined.

In these methods a polynucleotide is prepared, which is complementary to the nucleic acid sequence, which characterizes the organism or its antibiotic resistance and which additionally includes one or more modified nucleotides according to the invention. This polynucleotide is hybridized with a nucleic acid obtained from the organism being studied. Failure to hybridize indicates absence of the organism or of the resistance characteristic. Hybridized nucleic acid duplexes are then identified by forming a complex between the duplex and a suitable polypeptide, which carries a detectable moiety, and detecting the presence of the complex using an appropriate detection technique. Positive detection indicates that the complex, the duplex and therefore the nucleic acid sequence of interest are present.

This approach can be extended to the diagnosis of genetic disorders, including, but not limited to, thalassemia and sickle cell anemia. The deoxyribonucleotide acid gene sequence whose presence or absence (in the case of thalassemia) is associated with the disorder can be detected following hybridization with a polynucleotide probe according to this invention based upon complex formation with a suitable detectable polypeptide.

The mapping of genes or their transcripts to specific loci on chromosomes is a tedious and time consuming occupation, involving mainly techniques of cell fusion and somatic cell genetics. Although in situ hybridization has been employed successfully for mapping single copy gene sequences in species that undergo chromosomes polytenization, such as *Drosophila*, detection of unique sequence genes in most higher eukaryotic chromosomes has been difficult using standard hybridization methods. Since recombinant DNA technology has made feasible the molecular cloning of virtually every single-copy sequence found in eukaryotic cells, it would be extremely beneficial to have a rapid and sensitive method for mapping the chromosomal origin of such cloned genomic fragments.

Modified nucleotides may be used in a method of gene mapping by in situ hybridization, which circumvents the use of radioisotopes. This procedure takes advantage of a thymidine analog containing biotin that can be incorporated enzymatically into DNA probes by nick translation. After hybridization in situ the biotin molecules serve as targets for affinity purified anti biotin antibodies.

It has been found that polytene chromosomes could be used as a test system for establishing the efficacy of probes using the modified nucleotides according to the invention as detected by indirect immunofluorescence for in situ gene mapping. Many of these clones have already been assigned to specific bands on the *Drosophila* chromosome map by conventional in situ hybridization methods employing radioisotopes.

It has also been shown that this immunological method also works with mammalian chromosomes wherein satellite DNA has been mapped to the centromeric regions of mouse metaphase chromosomes. The result provides a basic foundation for the development of a simple gene mapping procedure for single copy (unique) sequences in chromosomes from human and other mammals. Such a procedure should greatly facilitate our understanding of the genetic organization of the chromosome and make clinical cytogenetic diagnosis much more rapid and practical.

While a single step "antibody sandwich" method in which the chromosome spread is challenged, post hybridization, with rabbit anti biotin IgG may succeed, this protocol may not generate sufficient fluorescence for unambiguous gene assignments. However, a much stronger fluorometric signal can be achieved by using the "haptene-antibody sandwich technique" described by Lamm et al., (1972); and Wofsy, et al., (1974). In this procedure the primary antibody (e.g., monospecific, rabbit anti biotin IgG) is chemically modified with a haptenization reagent, such as 2,4-dinitrofluorobenzene, preferably while the immunoglobulin is bound to an antigen affinity column (biotin Sepharose™). As many as 15-20 haptene (DNP) groups can be coupled to the primary antibody without decreasing its antigen binding affinity or specificity (See e.g., Wallace and Wofsy, 1979). If the primary antibody treatment of the test sample is followed by an incubation with a fluorescently labeled anti hapten IgG antibody, rather than a fluorescently labeled anti IgG, a 5-7 fold increase in fluorescence signal can be achieved. Since one also has available monospecific guinea pig anti DNP IgG, the secondary antibody can be haptenized with biotin and thus generate two anti-hapten IgG populations, DNP labeled anti-biotin IgG and biotin-labeled anti-DNP IgG. These can be used alternately to achieve several rounds of hapten-antibody sandwiching and then followed with fluorescently labeled protein A from *Staphylococcus aureus*, which binds specifically to IgG molecules from many mammalian species, and result in an enormous amplification of the primary antibody signal with its concomitant utility.

Polytene chromosomes hybridized with biotinized DNA probes can be incubated with streptavidin followed by a subsequent incubation with bovine serum albumin which has been doubly labeled with biotin and FITC (FITC, biotinyl-BSA). Since only one of the four streptavidin subunits is likely to be involved in binding at each biotinized DNA site, potentially one labeled BSA molecule can bind to each of the remaining three nonconjugated subunits of the streptavidin biotinyl nucleotide complex. The fluorescence signal from this single streptavidin+FITC, biotinyl-BSA layer will be compared with a control using the basic "antibody sandwich method."

If the "antibody sandwich" and streptavidin+FITC, biotinyl-BSA detection intensities are comparable, one can attempt to enhance the streptavidin+FITC, biotinyl BSA system to single copy copy sensitivity in a manner that parallels the multiple "haptene antibody sandwich" approach. Since some of biotin groups on BSA will not be bound to the first layer of streptavidin, a second layer of streptavidin can be added until sufficient signal is obtained. For example, if in the second layer, only two streptavidin protomers bind to each first layer BSA and each of these streptavidin protomers binds three FITC biotinyl BSA molecules, then the second layer intensity will be twice as great as that from the first layer; for the third layer, with analogous binding stoichiometries, the fluorescent intensity will be 12-fold that of the first layer, so the total intensity will rapidly increase. With successively added layers larger carrier protein such as thyroglobulin rather than BSA can be used in order to maximize amounts of attached fluorescent and biotin probes. It may also be necessary to use a longer linker arm between the biotin probe and the carrier protein. A longer linker arm should sterically optimize the theoretical delivery of a biotinized fluorescent carrier molecule to each nonconjugated streptavidin subunit and maximize the number of streptavidin protomers in the subsequent layer which will bind to the biotinized fluorescent carrier. Appropriate controls are done to insure that substitution of the carrier protein with fluorescent probes and biotin does not cause solubility and/or nonspecific binding problems.

The streptavidin-carrier protein delivery system has two significant advantages over the immunofluorescent approach in addition to its speed of delivery. First, only two protein components are needed to form the layers. Second, only the carrier protein needs to be modified and it is not necessary to maintain functional or even total structural integrity as long as the biotin groups are accessible to streptavidin.

An alternative to the fluorescence method for visualizing hybridized probes is to direct enzymes such as peroxidase, alkaline phosphatase of β-galactosidase to the hybridization site where enzymatic conversion of soluble substrates to insoluble colored precipitates permits light microscope visualization. The important advantage of this technique is that the histochemical methods are 10 to 100-fold more sensitive than fluorescence detection. In addition, the colored precipitates do not bleach with extensive light exposure thus avoiding one of the general disadvantages of fluorescent light microscopy. These enzymes can be coupled to the final antibody instead of fluorescent probes in the "haptene antibody sandwich" technique using bifunctional reagents such as glutaraldehyde or in the case of peroxidase via oxidation of the peroxidase carbohydrate moieties to aldehydes and coupling of these residues with C-amino groups of the desired protein. For the streptavidin biotinized carrier protein method, an enzyme with biotinyl groups coupled to it could replace a fluorescently biotinized carrier system. Alternately, the enzyme could be coupled via biotin to the last layer of streptavidin with amplification of streptavidin sites being built up in preceding layers using biotinized BSA or thyroglobulin.

Detecting and/or imaging very low levels of fluorescent light is possible using currently available image intensifiers or systems composed of lasers and photomultipliers. These methods permit the detection of light down to the level of individual photons. With suitable digital processing systems, images can be produced in which each point (i.e., each pixel) of the image is strictly proportional to the number of photons emitted by a point at the object. Using systems of this kind or flow systems in which the cells or parts of cells flow past a laser beam, one can obtain detection sensitivity increases for fluorescent material of factors between 100 and 1000 beyond that which can be detected by the eye. This increase is sufficient to detect the fluorescence of single copy genes.

5.3.5 Other Detection Techniques

Detectable labels of formula I can also be conjugated directly to signal generating compounds, for example, by conjugation with an enzyme or fluorophore. Illustrative enzymes of the invention include, but are not limited to, hydrolases, particularly phosphatases, esterases and glycosidases, oxidoreductases, and peroxidases. Illustrative fluorescent compounds of the invention include, but are not limited to, those disclosed in section 4.1.4 above and also include rhodamine and its derivatives, dansyl, and umbelliferone. Illustrative chemiluminescent compounds of the invention include, but are not limited to, luciferin and 2,3 dihydrophthalazinediones, for example, luminol.

Means of detecting labels are well known to those of skill in the art. For example, where the label is a fluorescent label, it can be detected by exciting the fluorochrome with the appropriate wavelength of light and detecting the resulting fluorescence, for example, by microscopy, visual inspection, via photographic film, by the use of electronic detectors such as charge coupled devices or photomultipliers and the like. Similarly, enzymatic labels can be detected by providing appropriate substrates for the enzyme and detecting the resulting reaction product. Finally, simple calorimetric labels are often detected simply by observing the color associated with the label. Thus, in various dipstick assays, conjugated gold often appears pink.

5.4 Phosphoramidite Synthesis

Another preferred class of reagents of the invention are phosphoramidite compounds that incorporate the detectable labels of the invention. Phosphoramidite reagents have the general structure:

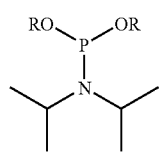

and are capable of forming a covalent bond with a hydroxyl group of a sugar (e.g., the 3' or 5' hydroxyl group) of a detectable label of the invention. Accordingly, the invention provides methods of making phosphoramidite compounds from any of compounds of formula I-XL, which comprise a phosphoramidite reagent at the 5'-OH or the 3'-OH. Such phosphoramidite reagents are particularly useful for the automated chemical synthesis of nucleic acids labeled with the detectable labels of the invention. Such phosphoramidite reagents, when reacted with a hydroxyl group, such as a 5'-hydroxyl group of a nucleoside or nucleotide or nucleic acid, form a phosphite ester linkage which, in turn, is oxidized to yield a phosphate ester linkage. For a detailed discussion of phosphoramidite chemistry see, e.g., Carruthers et al., U.S. Pat. Nos. 4,458,066 and 4,415,732 and Gait, 1985, *Oligonucleotide Synthesis: A Practical Approach*, IRL Press, Oxford, England, each of which is incorporated herein by reference. The phosphoramidite reagents can be nucleosidic or non nucleosidic.

5.5 Detectable Label-Containing Oligonucleotides

The invention further provides oligonucleotides comprising the detectable labels of the invention. One or more of the nucleotides in the oligonucleotides can be a ribonucleotide or a nucleotide analog. An oligonucleotide of the invention can be of any length, but is preferably at least 8 nucleotides long. In other embodiments, an oligonucleotide of the invention is 10, 12, 15, 18, 20 or more nucleotides in length. In certain embodiments, the oligonucleotide is less than 50, less than 40, or less than 30 nucleotides in length.

Oligonucleotides of the invention can typically form complementary base pairing and give an —OH group serving as the origin of synthesis of complementary chain at the 3' terminus. Accordingly, its backbone is not necessarily limited to the one via phosphodiester linkages. For example, it may be composed of a phosphorothioate derivative having S in place of O as a backbone or a peptide nucleic acid based on peptide linkages.

In general, detectable labeled oligonucleotides can be synthesized with a variety of different solid supports including, but not limited to, controlled pore glass or polystyrene.

5.6 Methods Utilizing Detectable Labels

Several hybridization assay formats that employ detectable labels as a means for detecting hybridization have been described, some of which are described below. These assays are useful for, e.g., detecting the presence of a specific nucleotide sequence in a sample, detecting the presence of contiguous sequences on a target nucleic acid, for detecting the presence of mutations within a target nucleic acid sequence, monitoring the kinetics of nucleic acid hybridization, and monitoring the progression of PCR reactions. It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary," unless otherwise indicated, refers to an oligonucleotide that forms a stable duplex with its "complement" under assay conditions, generally where there is about 90% or greater homology.

5.6.1 Detection of Target Nucleic Acids

Described herein are exemplary embodiments that employ detectable labels of the invention for detection of nucleic acid hybridization events.

While the assay formats described herein are represented in terms of systems employing only a single detectable label, multi-reporter systems may also be practiced. Such multi-reporter systems are advantageous in applications requiring the analysis of multiple hybridization events in a single reaction volume. In such systems, each of the reporter molecules produces an emission that is spectrally resolvable among the emissions of the other reporters.

5.6.1.1 Probe Methods

In one assay format, a single oligonucleotide probe is used. The probe comprises a detectable label of the invention. The detectable label can be attached to the 3' end of the probe or the 5' end, or can be at any nucleotide within the probe sequence.

The basic principles of oligonucleotide probe design and synthesis are well known. Those basic principles apply generally to the design and synthesis of oligonucleotide probes used in this invention.

The invention includes an essentially unlimited number of different oligonucleotide probes. For example, an oligonucleotide probe used according to this invention can vary considerably in length. The preferred length will depend on considerations such as the target nucleic acid length, length of the nucleotide sequence of interest, target nucleic acid type (i.e., DNA or RNA), target nucleic acid G-C content, and the spacing of the detectable label on the probe. Preferably, the length of the probe used in practicing this invention is from 20 to 200 nucleotides. More preferably, the length is from 40 to 100 nucleotides.

Regardless of probe length, the probe can vary in nucleotide sequence. The nucleotide sequence of a probe used in this invention will depend on the sequence of the target nucleic acid. The probe's nucleotide sequence should have sufficient complementarity to the target nucleic acid to allow hybridization with the target nucleic acid under the chosen in situ hybridization conditions. Preferably, base pair matching between the probe and target nucleic acid is at least 80%. More preferably, the base pair matching is approximately 100%.

The total number, and the spacing, of the detectable label in the oligonucleotide can vary. Preferably, a detectable label is incorporated within five bases from the 3' end of the oligonucleotide.

5.6.1.2 5'→3' Exonuclease Assay

In yet another assay format, referred to herein as the 5'-3' exonuclease assay, a doubly labeled probe including both a reporter label such as, for example, a fluorophore, and a quencher label, such as, but not limited to, tetramethylrhodamine, Black Hole Quenchers (BioSearch Technologies, Novato, Calif.), DABCYL, or QSY-4, is digested upon hybridization to a target nucleic acid, thereby liberating one or both of the labels from the probe (Lee et al., 1993, *USA*, 88:7276-7280; U.S. Pat. Nos. 5,538,848 and 5,210,015, which are incorporated herein by reference). In the methods of the invention, either the fluorophore or the quencher or both can be incorporated into an oligonucleotide using a detectable label of the invention. In this method, the doubly labeled probe is hybridized to a target nucleic acid. In addition, an oligonucleotide primer is hybridized to the target nucleic acid at a position upstream from the probe, i.e., in the 5' direction relative to the probe and closer to the 3'-end of the target nucleic acid. The primer is then extended using a polymerase enzyme having 5'→3' exonuclease activity, e.g., a DNA polymerase, thereby forming an extended primer. During the primer extension reaction, the 5'→3' exonuclease activity of the polymerase serves to digest the probe so as to form a first probe fragment including the reporter label and a second probe fragment including the quencher label. Thus, the reporter and quencher labels are separated, and the emission of the reporter becomes unquenched. This process can be performed using TaqMan® kits and reagents available from Roche Molecular Diagnostics, Pleasanton, Calif.

5.6.1.3 Real-Time PCR

The assays described herein may be conducted in combination with a nucleic acid amplification step, e.g., PCR. That is, prior to conducting the hybridization assay, all or part of the nucleic acid sample may be amplified. When performed in combination with an amplification step, the hybridization assay may be conducted in an end-point mode or a real-time mode. In an end-point mode, the hybridization assay is performed after the amplification reaction is complete, e.g., after all or substantially all of the amplification cycles of a PCR reaction have been completed. In a real-time mode, a hybridization assay is performed multiple times during the amplification reaction, for example, after each thermocycle of a PCR process (Higuchi, U.S. Pat. Nos. 5,994,056 and 6,171,785, each of which is incorporated herein by reference). The real time mode is preferred when a quantitative measure of the initial amount of target nucleic acid is required, e.g., where the copy-number of pathogen nucleic acid present in a blood sample.

5.6.1.4 Detection of Ribonuclease Activity

Detectable label-containing nucleic acids can also be used to detect the presence and/or amount of RNase activity in a sample.

Briefly, ribonuclease activity is detected by incubating a synthetic oligonucleotide that serves as the RNase substrate with the sample, for a time sufficient for cleavage of the substrates by a ribonuclease enzyme. The substrate comprises a single stranded nucleic acid molecule containing at least one ribonucleotide residue at an internal position that functions as a cleavage site, a reporter dye on one side of the cleavage sites, and a quencher dye on the other side of the cleavage site. Upon cleavage of the internal ribonuclease residue, the reporter dye, whose emission was quenched by the quencher dye, becomes detectable. Thus, detection of a fluorescence signal indicates that a ribonuclease cleavage event has occurred, and, therefore, the sample contains ribonuclease activity.

In one embodiment, the RNase detection methods of the invention are conducted in conjunction with one or more positive controls. In one embodiment, the positive control is a quantitative positive control.

5.6.1.5 Detection of Endonuclease Activity

Detectable label-containing, nucleic acids can also be used to detect the presence and/or amount of endonuclease activity in a sample.

Briefly, endonuclease activity is detected by incubating a labeled oligonucleotide with the sample, for a time sufficient for cleavage of the substrates by an endonuclease enzyme, or other molecule having endonucleolytic activity. The substrate comprises a single stranded nucleic acid molecule containing at least one deoxyribonucleotide residue at an internal position that functions as a cleavage site, a reporter dye on one side of the cleavage sites, and a quencher dye on the other side of the cleavage site. Upon cleavage of the internal ribonuclease residue, the reporter dye, whose emission was quenched by the quencher dye, becomes detectable. Thus, detection of a fluorescence signal indicates that an endonucleolytic cleavage event has occurred, and, therefore, the sample contains endonuclease activity.

In one embodiment, the endonuclease detection methods of the invention are conducted in conjunction with one or more positive controls. In one embodiment, the positive control is a quantitative positive control.

5.6.1.6. Detection of TdT Activity

Detectable label-containing nucleic acids can also be used to detect the presence and/or amount of terminal deoxynucleotidyl transferase (TdT) activity in a sample.

Briefly, TdT activity is detected by incubating an unlabeled oligo- or polynucleotide with the sample in the presence of a nucleotide triphosphate bearing a label, for a time sufficient for addition to the substrate of one or more labeled nucleotide triphosphates by TdT enzyme, or other molecule having TdT activity. The substrate comprises a single- or double-stranded nucleic acid molecule containing at least one free 3' OH group. The addition of the label to the substrate can be detected upon separation of the oligo- or polynucleotide from the labeled nucleotide triphosphate.

In one embodiment, the TdT detection methods of the invention are conducted in conjunction with one or more positive controls. In one embodiment, the positive control is a quantitative positive control. In one embodiment, the oligo- or polynucleotide is labeled at an internal site with a quencher, and the labeled nucleotide triphosphate bears a fluorescent molecule as a label. In another embodiment, the oligo- or polynucleotide is labeled at an internal site with a fluorophore, and the labeled nucleotide triphosphate bears a quencher molecule as a label. In either of the above two embodiments, addition of the labeled nucleotide triphosphate enables real-time detection of the TdT activity. Such an assay requires that the label on the oligo- or polynucleotide is positioned such that fluorescence resonant energy transfer (FRET) can occur between the quencher and the fluorophore.

5.6.1.7 Chromosomal Karyotyping

The invention also provides a method of chromosomal karyotyping. In this method, modified polynucleotides are prepared which correspond to known genes and include modified nucleotides. These polynucleotides are hybridized with chromosomal deoxyribonucleic acid and the resulting duplexes contacted with appropriate polypeptides under suitable conditions to permit complex formation. The polypeptides include detectable moieties so that the location of the complexes can be determined and the location of specific genes thereby fixed.

5.6.1.7 Detection of Tumor Cells

Tumor cells can be diagnosed by preparing polynucleotides, which are modified according to this invention and are complementary to the messenger ribonucleic acid synthesized from a deoxyribonucleic acid gene sequence associated with the production of polypeptides, such as α-fetal protein or carcinoembryonic antigen, the presence of which is diagnostic for specific tumor cells. Hybridization and detection of hybrid duplexes thus would provide a method for detecting the tumor cells.

5.7 Kits

The present invention further provides kits comprising the compositions of the invention. Such kits can be useful, inter alia, for practicing the methods described herein, or to provide materials for synthesis of the compositions described herein. Generally, a kit of the invention comprises in one or more containers a detectable label of the invention or an oligonucleotide that incorporates a detectable label of the invention. Additional components can be included in the kit, depending on the particular application that utilizes the compounds of the invention.

For example, where the kit is directed to the real time PCR assays described in Section 5.6.1.3, the kit may further comprise a DNA polymerase. Where a kit of the invention is intended for the practice of the RNase detection assays of Section 5.6.1.4, the kit may further comprise, for example RNase-free water. Where the kit is directed to end-labeling a double- or single-stranded DNA molecule, the kit can further comprise a terminal deoxynucleotidyl transferase. Where the kit is directed to assaying an enzyme activity, such as endonuclease activity or terminal deoxynucleotidyl transferase activity, the kit can further contain a standard amount of endonuclease or terminal deoxynucleotidyl transferase, respectively, of a known specific activity.

Such kits may optionally contain one or more of: a negative and/or positive control, a buffer, and instructions for use of the kit's reagents. Where the kit is intended for diagnostic applications, the kits may further include a label indicating regulatory approval for the diagnostic application.

5.8 General Synthesis of Detectable Labels

The invention will be further clarified by a consideration of the following illustrative examples, which are intended to be purely exemplary of the invention and not to in any way limit its scope.

The compounds of the invention can be obtained via the synthetic methodology illustrated in Schemes 1-5. Starting materials useful for preparing the compounds of the invention and intermediates thereof, are commercially available or can be prepared from commercially available materials using known synthetic methods and reagents.

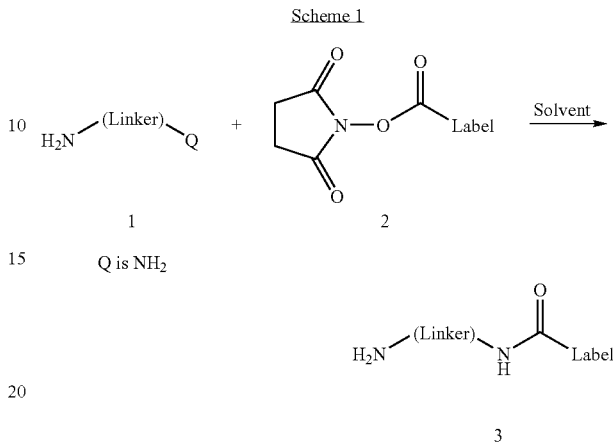

Scheme 1

Scheme 1 outlines a method useful for synthesizing compounds comprising a linker and a label, wherein linker is for example, but not limited to, polyethylene glycol or polymethylene and label is a colorimetric, chemiluminescent, bioluminescent, or fluorescent emitting compound.

First, the carboxyl group of compound 2 is substituted with a N-hydroxysuccinimide (NHS) group to facilitate amidation and peptide coupling. However, other suitable coupling groups are well known in the art, for example, but not limited to 1-[bis(dimethylamino)methylene]-hexafluorophosphate-1,3-oxide-O-(benzotriazol-1-yl)N,N,N',N'-tetramethyluronium-hexafluorophosphate (HBTU), dicyclohexylcarbodiimide (DCC), or O-(7-azabenzotriazol-1-yl) 1,1,3-,3-tetramethyluronium hexafluorophosphate (HATU). Diamines 1, wherein, for example, the linker is tetraethyleneglycol or tetramethyleneglycol, are available commercially (e.g., Aldrich Chemical Co., Milwaukee, Wis.). In addition, Q can be SH or OH, in which case the amine can optionally be protected. Organic solvents suitable for the conversion of compound 1 to compound 3 include, but are not limited to, dichloromethane, diethyl ether, tetrahydrofuran, benzene, toluene, xylene, hydrocarbon solvents (e.g., pentane, hexane, and heptane), and mixtures thereof. After addition of compound 1 to compound 2, the reaction mixture is allowed to stir for about 2 days, and the reaction mixture is allowed to stir until the reaction is substantially complete as determined by using an appropriate analytical method, preferably thin layer chromatography or high performance liquid chromatography. Then the reaction mixture is quenched by methods known in the art and compounds 2 can be isolated by work up and purified if desired by methods known in the art, for example, column chromatography or preparative HPLC.

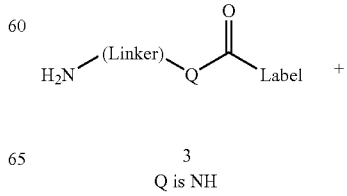

Scheme 2

-continued

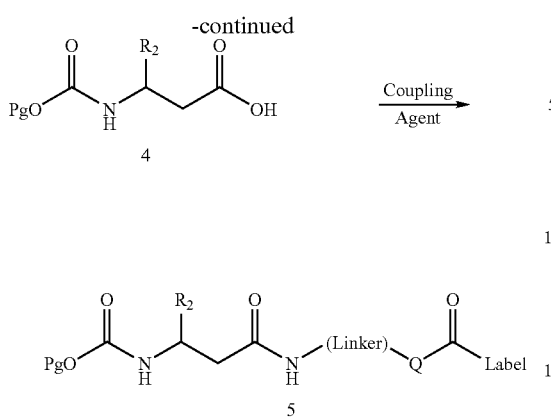

Scheme 2 illustrates the coupling of the linker label compound 3 with the $R_2$-substituted compound 4 to form the -linker-label compound 5, wherein $R_2$ is described herein and -Pg is a protecting group.

Preferably, to synthesize compound 5, a solution of about 1 equivalent of 4 and 1.5 equivalents of 3 is dissolved in a suitable organic solvent under an inert atmosphere. The use of polar aprotic solvents (e.g., dimethylformamide, acetonitrile, or dimethyl sulfoxide) is preferred. The solution is maintained at a constant temperature within the range of about 15° C. to about room temperature, preferably at room temperature and base is added, preferably an amine base, such as, but not limited to, diisopropylethylamine. Preferably, about 10 equivalents of the substituted amine is added in one single addition. After addition of the amine base, the reaction mixture is allowed to stir for about 1 to about 4 hours at room temperature, preferably at a rate such that the reaction mixture temperature remains constant. The reaction mixture is allowed to stir at this temperature until the reaction is substantially complete as determined by using an appropriated analytical method, preferably thin-layer chromatography or high performance liquid chromatography. The reaction mixture is then quenched to afford a mixture containing compound 5. Compound 5 can purified by techniques known in the art (e.g., preparatory HPLC or flash chromatography). However, the crude preparation containing compound 5 could also be used in the next step without further purification.

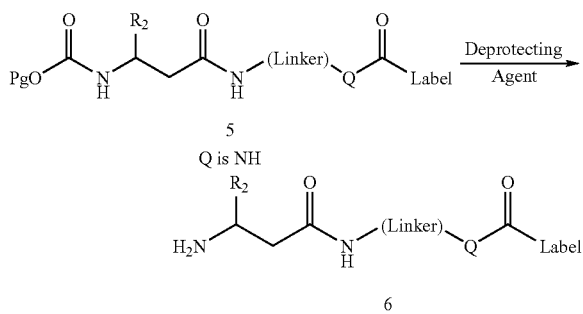

Scheme 3 outlines methods useful for deprotecting the substituted linker labeled compound 5. A typical procedure for deprotection involves dissolving compound 5 in a polar organic solvent. Organic solvents suitable for the conversion of compound 5 to compound 6 include, but are not limited to, methanol, dimethylformamide, acetonitrile, or dimethyl sulfoxide. After compound 5 is dissolved a deprotecting agent is added. Suitable deprotecting agents will remove the protecting group without reacting with any other moiety in the compound. Examples of suitable deprotecting reagents include, but are not limited to, piperidine, morpholine, and DBU. The reaction mixture is allowed to stir at room temperature until the reaction is substantially complete (e.g., about 12 hours) as determined by using an appropriate analytical method, preferably ninhydrin, thin layer chromatography, or high performance liquid chromatography. Then the reaction mixture is quenched and compound 6 can be isolated by work up and purified if desired by methods known in the art, for example, column chromatography or preparative HPLC.

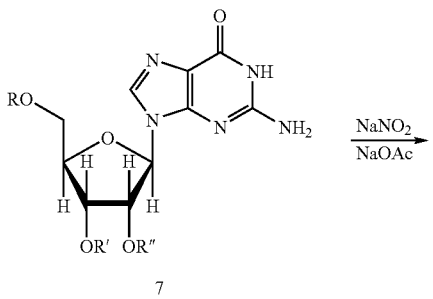

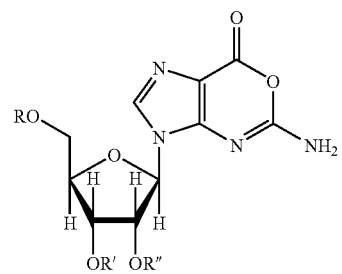

R, R', and R" are independently H, Protecting group, or mono-, di,- or triphosphate Purine sugar compounds of formula 7 can be converted to oxanosine sugar compounds of formula 8 by dissolving compound 7 in a buffer (e.g., sodium acetate) of pH 3-4 and sterile water at room temperature. Sodium nitrite is then added and the solution is stirred at room temperature. The reaction mixture is allowed to stir at room temperature until the reaction is substantially complete (e.g., about 24 hours) as determined by using an appropriate analytical method, preferably high performance liquid chromatography. The reaction mixture is then quenched and compound 8 can be isolated by work up and purified if desired by methods known in the art, for example, column chromatography or preparative HPLC. The compound can be further purified if desired by, for example, lyophilization with water.

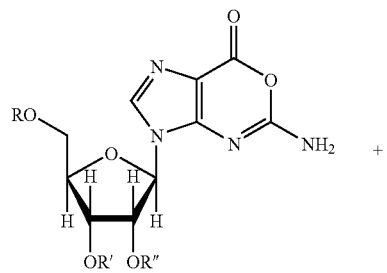

8

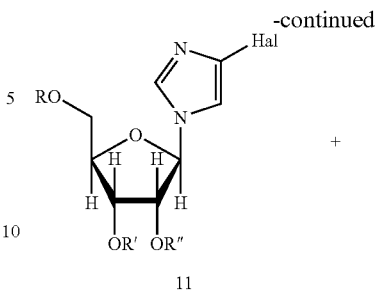

11

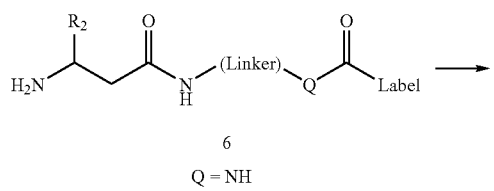

6
Q = NH

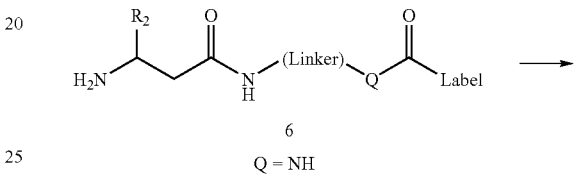

6
Q = NH

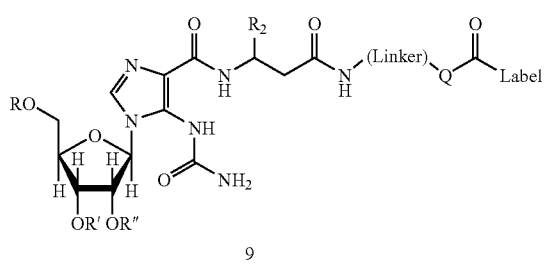

9

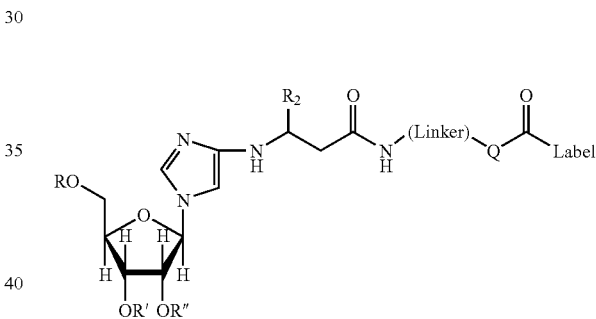

12

The detectable label compound 8 can be synthesized by contacting oxanosine compound 8 in a buffer (e.g., sodium borate) with substituted linker label compound 6 in sterile water. The reaction mixture is kept in an incubator with gentle stirring at 34° C. to 40° C. until the reaction is substantially complete (e.g., about 24 hours) as determined by using an appropriated analytical method, preferably high performance liquid chromatography. The reaction mixture is then quenched and compound 9 can be isolated by work up and purified if desired by methods known in the art, for example, column chromatography or preparative HPLC. The compound can be further purified if desired by, for example, lyophilization with water.

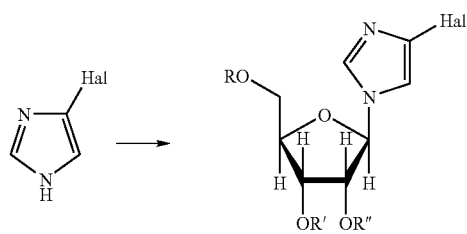

The detectable label 12 can be synthesized by first glycosylating a halogen substituted imidazole 10 to yield the glycosylated base 11 using methods known in the art, for example, 1995, *Nucl. Acid Res,* 23(4): 647-653 and 1996, *Tetrahedron Asymmetry,* 7(12): 3455-3464, each of which are incorporated herein by reference. Glycosylated base 11 is then contacted with substituted-linker-label compound 6 under conditions suitable for the formation of detectable label 12. See, e.g., 2000, *J. Heterocyclic Chemistry,* 37 (1): 119-126; 1987, *Australian J. Chemistry,* 40(8): 1399-1413; 1977, *Khim. Farm. Zh.,* 11(10): 38-42; 2000, *Chemistry of Heterocyclic Compounds,* 36(2): 182-184; 1982, *Indian J. Chemistry,* Sect. B, 21B(10): 928-640, each of which is incorporated herein by reference. Detectable label 12 can be purified if desired by methods known in the art, for example, column chromatography or preparative HPLC. The compound can be further purified if desired by, for example, lyophilization with water.

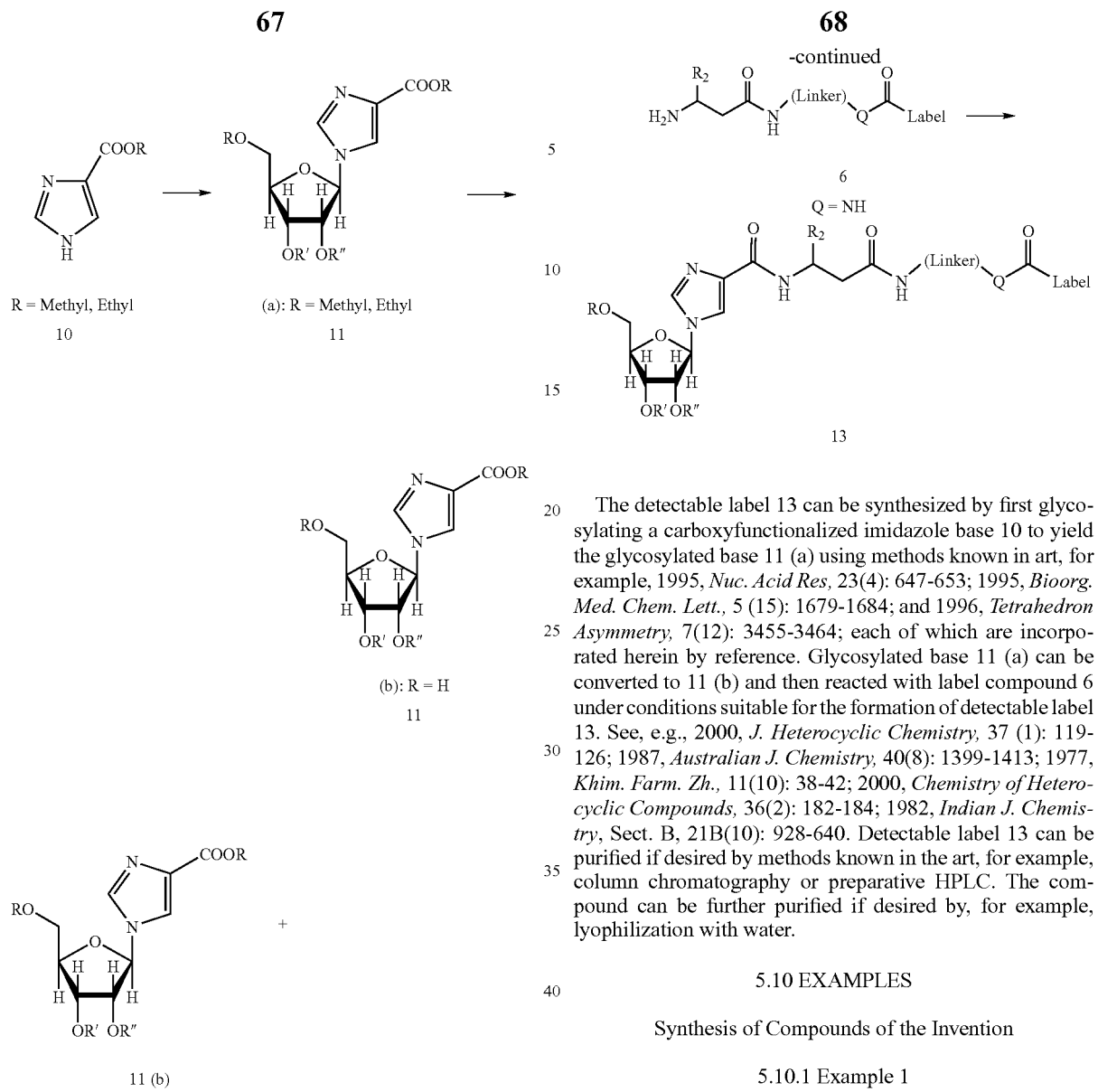

The detectable label 13 can be synthesized by first glycosylating a carboxyfunctionalized imidazole base 10 to yield the glycosylated base 11 (a) using methods known in art, for example, 1995, *Nuc. Acid Res*, 23(4): 647-653; 1995, *Bioorg. Med. Chem. Lett.*, 5 (15): 1679-1684; and 1996, *Tetrahedron Asymmetry*, 7(12): 3455-3464; each of which are incorporated herein by reference. Glycosylated base 11 (a) can be converted to 11 (b) and then reacted with label compound 6 under conditions suitable for the formation of detectable label 13. See, e.g., 2000, *J. Heterocyclic Chemistry*, 37 (1): 119-126; 1987, *Australian J. Chemistry*, 40(8): 1399-1413; 1977, *Khim. Farm. Zh.*, 11(10): 38-42; 2000, *Chemistry of Heterocyclic Compounds*, 36(2): 182-184; 1982, *Indian J. Chemistry*, Sect. B, 21B(10): 928-640. Detectable label 13 can be purified if desired by methods known in the art, for example, column chromatography or preparative HPLC. The compound can be further purified if desired by, for example, lyophilization with water.

5.10 EXAMPLES

Synthesis of Compounds of the Invention 5.10.1 Example 1

Synthesis of Biotin-PEG-Amine

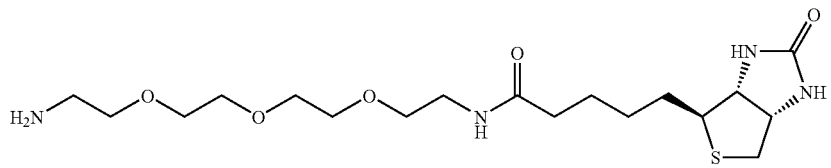

A 2.0 L round bottom flask was charged with tetraethyleneglycol diamine (7.0 g, 36.4 mmol) (commercially available from Molecular BioSciences; Boulder, Colo.) and dichloromethane (600 ml). To this clear solution was added a suspension of Nhydroxysuccinimide ("NHS") biotin (2.73 g, 8.0 mmol) (commercially available from Molecular BioSciences) in dichloromethane (100 ml) over a period of 50 minutes. The reaction was allowed to stir at room temperature for two days. The solvent was removed on the rotary evaporator under reduced pressure and the product was purified by colurmn chromatography (70% yield).

5.10.2 Example 2

Synthesis of FMOC-methyl-PEG-Biotin

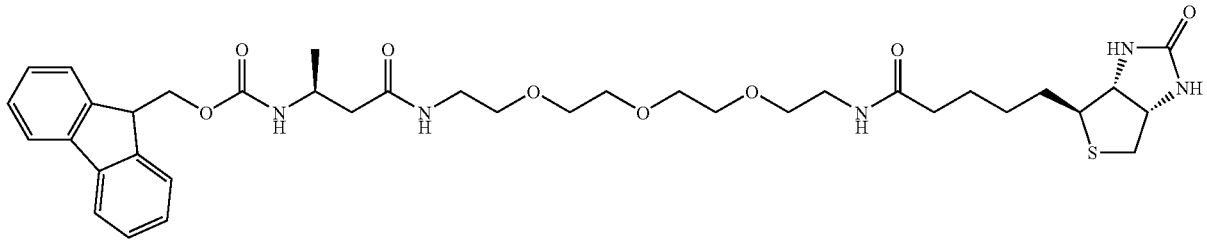

To a solution of FMOC-homoalanine (0.65 g, 2.0 mmol) (commercially available from Fluka), biotin PEG amine (0.56 g, 1.34 mmol) in DMSO DMF (6 ml, 5:1 ratio) was added HBTU in DMF (5 ml, 1.0 mmolar solution) under cooling condition. After 5 minutes of stirring N,N-diisopropylethylamine (1.0 ml) was added and the reaction mixture was stirred for 1.0 hr at room temperature. The solvent was evaporated under reduced pressure and the product was purified by column chromatography (50% yield).

5.10.3 Example 3

Synthesis of Methyl-PEG-Biotin

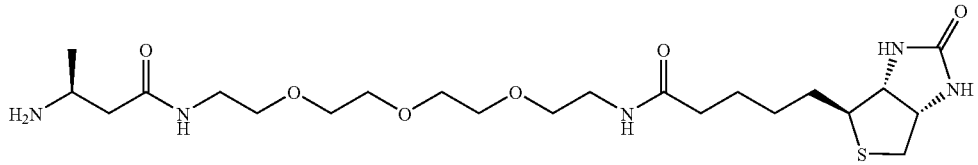

The FMOC protecting group was removed from amine using 1, 8 diazabicyclo [5.4.0]-undec-7-ene (DBU). To the solution of FMOC homoalanine PEG biotin (0.25 g, 0.345 mmol) in methanol was added DBU (0.2 g, 1.31 mmol) at room temperature and reaction was stirred overnight. Methanol was removed under vacuum and the product was purified by column chromatography (87% yield).

5.10.4 Example 4

Synthesis of Oxanosine Triphosphate

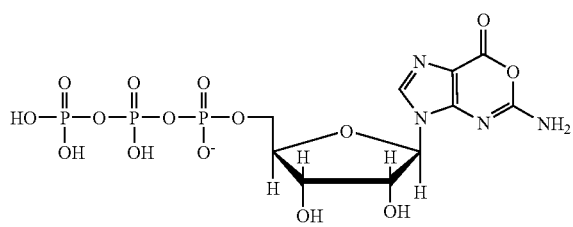

Guanosine triphosphate (210 mg, 0.384 mmol, lithium salt) (commercially available from Sigma, St. Louis, Mo.) was dissolved in a solution of sodium acetate buffer (2 ml, 12 M, pH 3.7) and sterile water (4 ml) at room temperature. To this clear solution was added sodium nitrite (50 mg, 0.724 mmol, 1.88 equiv) in sterile water (2 ml) at room temperature with gentle stirring and the reaction left for 24 hours. Analytical HPLC of this reaction showed one major (xanthosine) and one minor (oxanosine) peak and no detectable starting material. The compound was purified using a preparative column (Zorbax, SB-C18, 21.2 mm×25 cm, Part #880975-102) (commercially available from Agilent Technologies (Palo Alto, Calif.). The collected fractions containing the suspected product were pooled together and lyophilized. The purified oxanosine triphosphate was obtained as a white solid (42 mg, 21% yield) after two lyophilizations with water.

5.10.5 Example 5

Synthesis of α-methyl-PEG-Biotin Imidazole Triphosphate

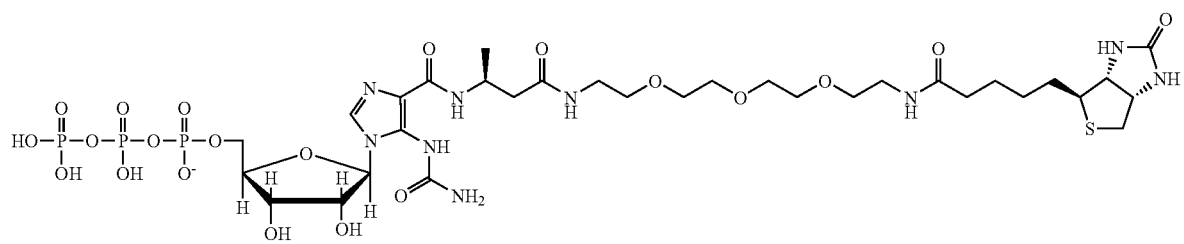

To a solution of oxanosine triphosphate (15 mg, 0.0286 mmol) in sodium borate buffer (12 ml, 250 mM, pH 9.0) was added methyl-PEG-biotin (20 mg, 0.0398 mmol, 1.39 equiv) in sterile water (1.0 ml). This reaction mixture was kept in an incubator at 38° C. for 24 hours with gentle movement using a shaker. The reaction mixture was analyzed by HPLC and found desired product, significant amount of oxanosine and some amine. The compound was purified by RP-HPLC (Symmetry Semi prep column, C-18, 7.8×300 mm, Part # WAT 066235, from Waters Corporation, Milford, Mass.) and isolated 11 mg (40% yield).

5.10.6 TdT Labeling with Imidazole-PEG-Biotin

The detectable labels of the invention include, but are not limited to, non radioactive ribonucleotide analogs purified by reverse phase HPLC and quantified by molecular mass. The detectable labels can be used, for example, as a substrate for terminal deoxynucleotidyl transferase (TdT). As an illustrative example imidazole-PEG-biotin can be transferred to the 3' hydroxyl terminus of double or single stranded DNA molecules for template independent biotinylation. DNA fragments labeled with imidazole-PEG-biotin hybridize efficiently to oligonucleotide microarrays and can readily be detected via staining with streptavidin fluorescent dye conjugates.

5.10.7 Fragmentation and Labeling

Genomic DNA samples (50 ng in 10 mM TRIS buffer, pH 8.3) were mixed with a master mix, $MgCl_2$, and a set of primers appropriate for amplifying a desired set of CYP450 polymorphisms. The master mix contained the following components: TRIS HCl buffer, pH 8.3; ammonium sulfate; KCl; DNA polymerase, uracil-N-glycosylase, and each of the deoxynucleotide triphosphates dATP, dCTP, dTTP, dGTP and dUTP. The reaction was subjected to the following thermocycling profile: 50° C. for 2 minutes, 95° C. for 10 minutes, 35 cycles of 95° C. for 15 sec., 67° C. for 4 minutes, followed by an incubation of 7 minutes at 72° C., and held at 4° C.

An aliquot of amplicons from the PCR reaction product from the PCR reaction was incubated with the mixture of DNase I and phosphatase to cleave amplicons to 25-100 bp length and dephosphorylate dNTPs in PCR mixture. Fragmented amplicons were subsequently labeled with imidazole-PEG-biotin by TdT.

5.10.7.1 DNase I Fragmentation Reaction

PCR reaction products were combined with a DNase fragmentation reagent containing DNase I, EDTA, alkaline phosphatase, and water. The mixture was incubated at 25° C. for 20 minutes, then 95° C. for 10 minutes. The fragmented amplicons were then held at 4° C. prior to initiating the TdT reaction.

5.10.7.2 TdT Labeling Reaction

The DNase fragmented amplicons were then incubated with the labeling mixture including TdT buffer (1M potassium cacodylate, 250 mM Tris base, 10 mM $CoCl_2$, and 0.2 mM DTT, pH 7.6), imidazole PEG biotin, TdT, water and stirred at 37° C. for 1 hour, then 95° C. for 5 minutes. The imidazole-PEG-biotin labeled amplicons were then held at 4° C. prior to transfer to hybridization solution.

5.10.8 Microarray Hybridization

The labeled amplicon was subsequently transferred to microarray hybridization buffer (SSPE, Triton X-100, standardization oligonucleotide, Denhardt's solution, and deionized water.

The denatured sample was loaded onto a fluidics station for 30 minute hybridization at 45° C. followed by 50° C. washes, 10 minute staining with streptavidin phycoerythrin and washed at room temperature. The microarray was scanned by a laser to generate fluorescent intensity values that are converted by software into genotype calls. Hybridization performance with PEG-biotin imidazole compound was monitored by several metrics: background intensity (BG), chip intensity values: key perfect match (KeyPM for key mutation sites) and reference perfect match (RefPM), pass rates (key and reference), and discrimination ratios for key mutation sites.

To assess the transfer efficiency and functional performance of imidazole PEG-biotin on microarrays, two clinical samples and a control sample were labeled with varying amounts of TdT (200, 400, and 800 units) in the presence 250 μM imidazole-PEG-biotin.

TABLE 1

| Amount of TdT | Sample | KeyPM Int | RefPM Int | BG | KeyPass Rate | RefPass Rate |
|---|---|---|---|---|---|---|
| 800 U | Control[1] | 832.24 | 734.49 | 166.63 | 96.3% | 91.4% |
| | A[2] | 1160.80 | 1021.64 | 87.23 | 98.1% | 93.9% |
| | B[2] | 705.93 | 559.19 | 80.81 | 100% | 92.0% |
| 400 U | Control | 689.06 | 584.20 | 82.33 | 100% | 91.9% |
| | A | 926.92 | 812.97 | 82.20 | 97.2% | 92.9% |
| | B | 637.59 | 517.60 | 81.61 | 97.2% | 92.0% |
| 200 U | Control | 412.43 | 355.46 | 80.02 | 85.2% | 75.3% |
| | A | 824.73 | 723.47 | 83.45 | 95.4% | 91.0% |
| | B | 499.68 | 414.32 | 104.86 | 98.1% | 91.4% |

[1]The control is genomic DNA sample and is commercially available from Coriell Cell Repository, reference # GM 09912.
[2]Sample A and B are clinical samples of CYP2Dss26 gene duplication.

Table 1 shows the efficiency of labeling nucleosides with imidazole PEG biotin labels. Particularly, Table 1 illustrates the efficiency of imidazole PEG biotin labels in detection of CYP450 polymorphisms.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications, patents and patent applications are cited herein, the disclosures of which are incorporated by reference in their entireties.

What is claimed is:

1. A compound of formula II:

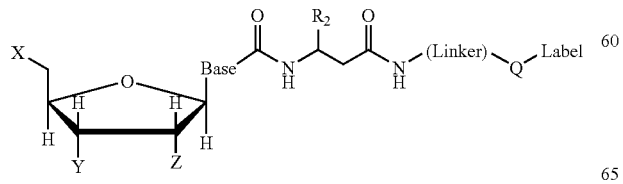

II alone or in combination with a counterion thereof or a stable salt, solvate, clathrate or mixture thereof, wherein:

base is

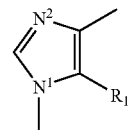

wherein sugar is covalently bonded to $N^1$ of the base;
wherein $R_1$ is —NHC(O)NH$_2$;
wherein $R_2$ is —H or alkyl;
each of X, Y, and Z is independently H, —OH, —O-alkyl, —SH, —SR$_4$, —NHR$_4$, —NR$_4$R$_5$,

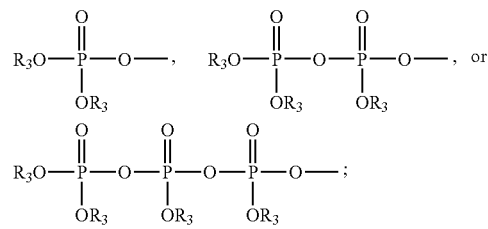

wherein $R_3$ is —H or metal;
$R_4$ is —H or alkyl;
$R_5$ is —H or alkyl;
linker is $(CH_2CH_2O)_nCH_2CH_2$, $(CH_2CH_2O)_n$, $(CH_2O)_n$ or $(CH_2)_n$;
wherein n is an integer from 1 to 30;
Q is O, S, or NH; and
label is a colorimetric compound, a chemiluminescent compound, a bioluminescent compound, a fluorescent compound, a non- or weakly fluorescent compound, or a quencher.

2. The compound of claim 1, wherein at least one of X, Y, and Z is —OH.

3. The compound of claim 1, wherein each of X, Y, and Z is —OH.

4. The compound of claim 1, wherein at least one of Y and Z is —OH and X is

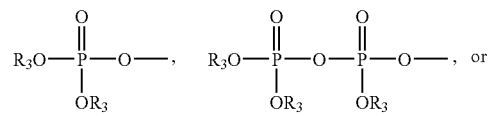

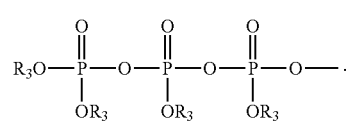

5. The compound of claim 1, wherein X is

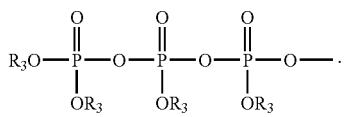

6. The compound of claim 1, wherein X is

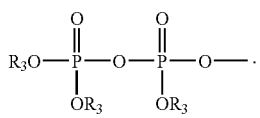

7. The compound of claim 1, wherein X is

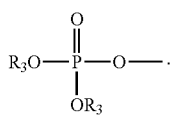

8. The compound of claim 1, wherein the linker is $(CH_2CH_2O)_n$, wherein n is an integer between 1 and 10.

9. The compound of claim 1, wherein the label is biotin, a biotin derivative or a fluorophore.

10. The compound of claim 1, wherein the fluorophore is fluorescein, tetrachlorofluorescein, hexachlorofluorescein, a non or weakly fluorescent compound, Cy3, Tetramethylrhodamine, Cy3.5, Carboxy-x-rhodamine, Texas Red, Cy5, Cy5.5, phycoerythrins, or allophycocynanins.

11. The compound of claim 1, wherein the label is

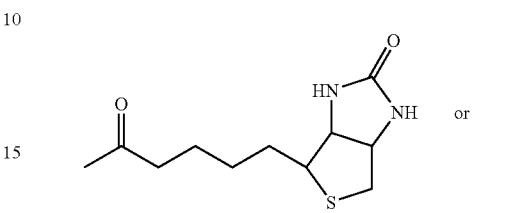

or

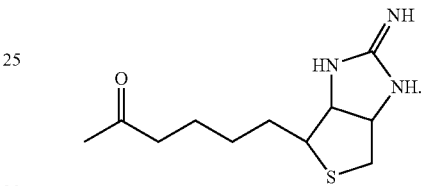

12. A compound of formula III:

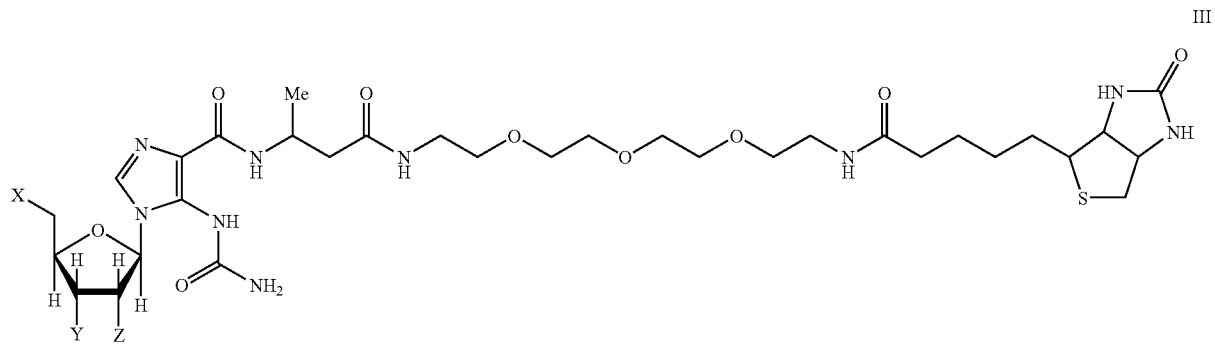

alone or in combination with a counterion thereof or a stable salt, solvate, clathrate or mixture thereof, wherein each of X, Y, and Z is independently —H, —OH, —O(alkyl), —SH, —SR$_4$, —NHR$_4$, —NR$_4$R$_5$,

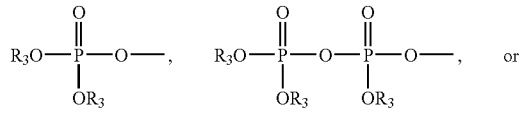

-continued

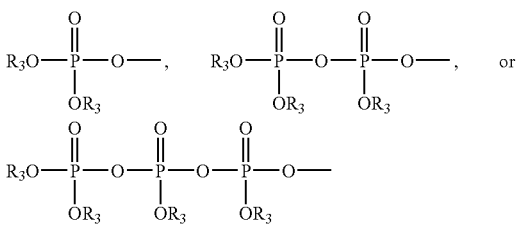

wherein R$_3$ is —H or metal; R$_4$ is —H or alkyl; and R$_5$ is —H or alkyl.

13. A compound of formula IV:

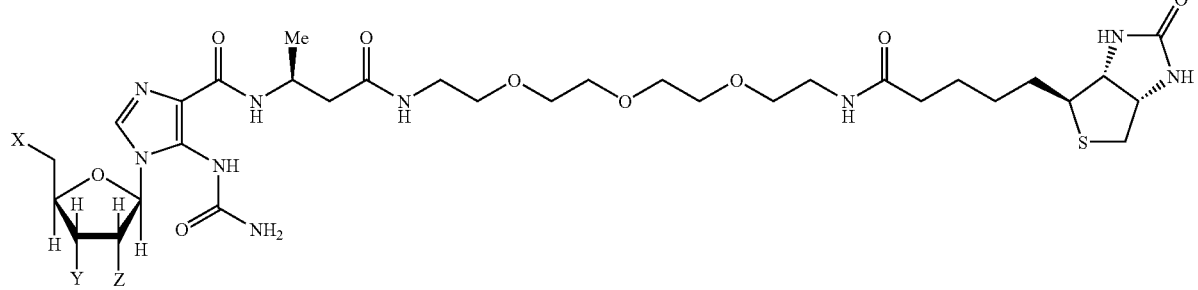

IV wherein X, Y, and Z are independently H, OH,

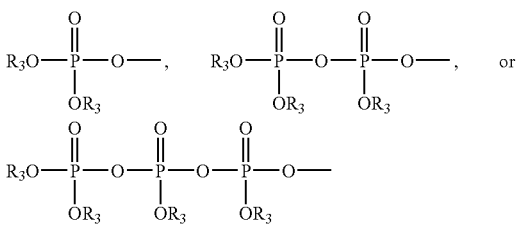

wherein R$_3$ is H or metal.

14. A compound of formula V:

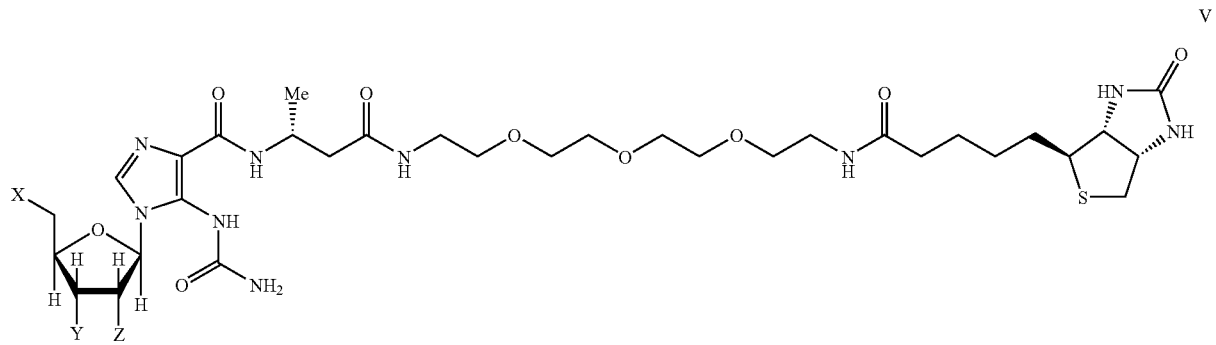

V wherein X, Y, and Z are independently H, OH,
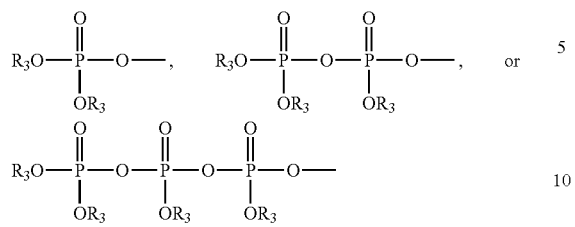
wherein $R_3$ is H or metal.
15. A compound of formula XV:
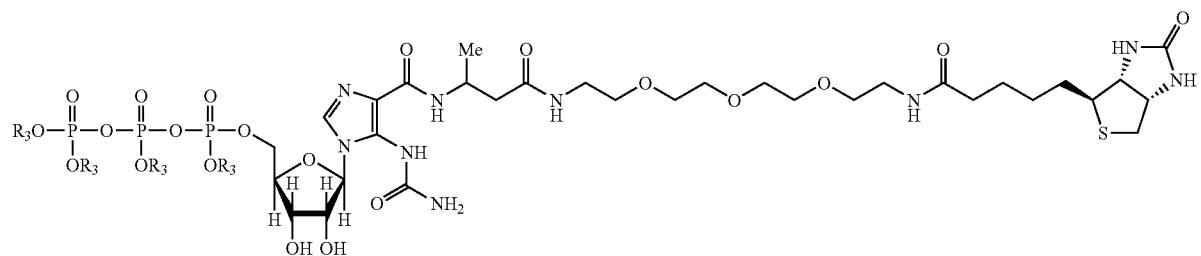
XV
wherein $R_3$ is H or metal.
16. A compound of formula XVI:
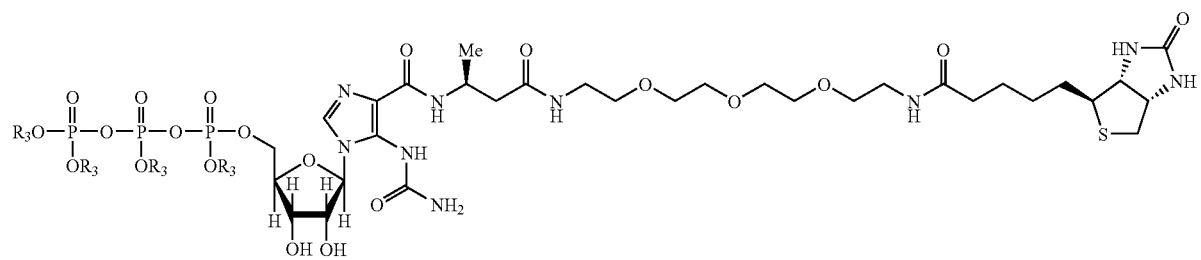
XVI
wherein $R_3$ is H or metal.
17. A compound of formula XVII:
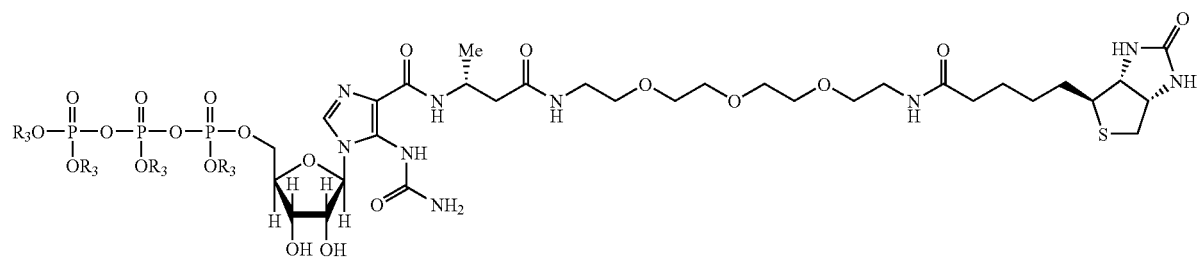
XVII
wherein $R_3$ is H or metal.
* * * * *